United States Patent
Noshi

(10) Patent No.: US 9,361,726 B2
(45) Date of Patent: Jun. 7, 2016

(54) MEDICAL IMAGE DIAGNOSTIC APPARATUS, MEDICAL IMAGE PROCESSING APPARATUS, AND METHODS THEREFOR

(71) Applicants: KABUSHIKI KAISHA TOSHIBA, Tokyo (JP); TOSHIBA MEDICAL SYSTEMS CORPORATION, Otawara-shi (JP)

(72) Inventor: Yasuhiro Noshi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 117 days.

(21) Appl. No.: 14/079,000

(22) Filed: Nov. 13, 2013

(65) Prior Publication Data
US 2014/0063011 A1  Mar. 6, 2014

Related U.S. Application Data

(63) Continuation of application No. PCT/JP2012/063078, filed on May 22, 2012.

(30) Foreign Application Priority Data

May 24, 2011 (JP) ................. 2011-115866

(51) Int. Cl.
| | | |
|---|---|---|
| G06T 15/08 | (2011.01) | |
| A61B 6/00 | (2006.01) | |
| H04N 13/02 | (2006.01) | |
| A61B 6/03 | (2006.01) | |
| A61B 5/055 | (2006.01) | |

(52) U.S. Cl.
CPC ............... *G06T 15/08* (2013.01); *A61B 6/461* (2013.01); *A61B 6/462* (2013.01); *A61B 6/503* (2013.01); *H04N 13/0275* (2013.01); *H04N 13/0282* (2013.01); *A61B 5/055* (2013.01); *A61B 6/03* (2013.01); *A61B 6/5288* (2013.01)

(58) Field of Classification Search
CPC .................. G06T 15/08; G06T 19/00; G06T 2207/30016; G06T 2207/30056; G06T 2207/30101; G06T 2207/10068; G06T 2207/20101; G06T 2200/04; G06T 2207/30012; G06T 2207/30096; G06T 2207/10088; G06T 2207/20092; G06T 1/0007; G06T 7/0012; G06T 2207/10116; G06T 2207/30048; G06T 2207/10072; G06T 2207/10081; G06T 2207/30061; G06T 7/0081; G06T 2207/10132; G06T 2207/20104; G06T 2207/30004; G06T 2207/30068; G06T 2200/02; G06T 2207/20108; G06F 19/3406; G06F 19/3418; A61B 5/055; A61B 6/032; A61B 6/504; A61B 8/469; A61B 6/03; A61B 8/483; A61B 8/585; A61B 6/548; A61B 6/466; A61B 6/469; A61B 5/0037; A61B 6/4021; A61B 6/02; A61B 6/022; A61B 8/523; A61B 8/463; G06K 9/3233
See application file for complete search history.

(56) References Cited

U.S. PATENT DOCUMENTS

| | | | | |
|---|---|---|---|---|
| 2004/0066555 | A1* | 4/2004 | Nomura ........................ | 359/462 |
| 2005/0083246 | A1 | 4/2005 | Saishu et al. | |
| 2008/0177172 | A1* | 7/2008 | John et al. .................... | 600/413 |
| 2009/0030314 | A1* | 1/2009 | Kawae ......................... | 600/443 |
| 2011/0043615 | A1 | 2/2011 | Saishu et al. | |
| 2011/0075900 | A1 | 3/2011 | Masumoto | |
| 2011/0144482 | A1* | 6/2011 | Sendai et al. ................ | 600/425 |
| 2011/0229005 | A1* | 9/2011 | Den Harder et al. ......... | 382/131 |
| 2012/0139911 | A1 | 6/2012 | Saishu et al. | |

FOREIGN PATENT DOCUMENTS

| | | |
|---|---|---|
| JP | 63-115543 | 5/1988 |
| JP | 2005-086414 | 3/2005 |
| JP | 2005-136726 | 5/2005 |
| JP | 2006-101329 | 4/2006 |

| | | |
|---|---|---|
| JP | 2008-073301 | 4/2008 |
| JP | 2010-99389 | 5/2010 |
| JP | 2011-092685 | 5/2011 |

OTHER PUBLICATIONS

International Search Report mailed Jul. 24, 2012 in PCT/JP2012/063078, filed May 22, 2012 (with English Translation).
Written Opinion of the International Searching Authority mailed Oct. 16, 2012 in PCT/JP2012/063078, filed May 22, 2012.

\* cited by examiner

*Primary Examiner* — Haixia Du
(74) *Attorney, Agent, or Firm* — Oblon, McClelland, Maier & Neustadt, L.L.P.

(57) ABSTRACT

According to an embodiment, in a medical image diagnostic apparatus, an accepting unit accepts input of conditions with respect to regions to be photographed and arrangement of the regions. An extracting unit extracts an area of interest of each subject by analyzing medical image data photographed based on the conditions accepted by the accepting unit. Based on the conditions and on the area of interest extracted by the extracting unit, a setting unit sets display conditions of a parallax image group to be displayed on a display unit having a stereoscopic viewing function.

7 Claims, 16 Drawing Sheets

| DIAGNOSIS REGION | REGION OF INTEREST | PARALLAX ANGLE | ROTATION | ROTATIONAL SPEED (deg/sec) | STOP (deg) | DIRECTION OF ROTATION | INITIAL POSITION (x, y, z) |
|---|---|---|---|---|---|---|---|
| LUNGS | MEDIASTINUM | 1° | YES | 30 | 360 | L TO R | (0, 100, 0) |
| | PERIPHERY | 3° | YES | 10 | 360 | L TO R | (0, 100, 0) |
| | LESIONED REGION | 2° | YES | 10 | 90 | L TO R | COORDINATES OF LESIONED REGION |
| HEART | . | . | . | . | . | . | . |
| | . | . | . | . | . | . | . |
| LIVER | . | . | . | . | . | . | . |
| | . | . | . | . | . | . | . |
| . | . | . | . | . | . | . | . |
| . | . | . | . | . | . | . | . |

TRANSITION PERIOD

FIG.17

| MODAL-ITY | DIAG-NOSIS REGION | REGION OF INTEREST | PARAL-LAX ANGLE | ROTA-TION | ROTA-TIONAL SPEED (deg/sec) | STOP (deg) | DIRECTION OF ROTATION | INITIAL POSITION (x, y, z) |
|---|---|---|---|---|---|---|---|---|
| X-RAY CT APPA-RATUS | LUNGS | MEDIASTINUM | 1° | YES | 30 | 360 | L TO R | (0, 100, 0) |
| | | PERIPHERY | 3° | YES | 10 | 360 | L TO R | (0, 100, 0) |
| | | LESIONED REGION | 2° | YES | 10 | 90 | L TO R | COORDINATES OF LESIONED REGION |
| | HEART | . | . | . | . | . | . | . |
| | | . | . | . | . | . | . | . |
| | LIVER | . | . | . | . | . | . | . |
| | | . | . | . | . | . | . | . |
| | . | . | . | . | . | . | . | . |
| | . | . | . | . | . | . | . | . |
| MRI APPA-RATUS | LUNGS | . | . | . | . | . | . | . |
| | | . | . | . | . | . | . | . |
| | HEART | . | . | . | . | . | . | . |
| | | . | . | . | . | . | . | . |
| | LIVER | . | . | . | . | . | . | . |
| | | . | . | . | . | . | . | . |
| | . | . | . | . | . | . | . | . |
| | . | . | . | . | . | . | . | . |
| . | . | . | . | . | . | . | . | . |

MEDICAL IMAGE DIAGNOSTIC APPARATUS, MEDICAL IMAGE PROCESSING APPARATUS, AND METHODS THEREFOR

CROSS-REFERENCE TO RELATED APPLICATIONS

This application is a continuation of International Application No. PCT/JP2012/063078, filed on May 22, 2012 which claims the benefit of priority of the prior Japanese Patent Application No. 2011-115866, filed on May 24, 2011, the entire contents of which are incorporated herein by reference.

FIELD

Embodiments described herein relate generally to a medical image diagnostic apparatus, a medical image processing apparatus, and methods therefor.

BACKGROUND

Conventionally, monitors are in practical use that enable a two-parallax image (binocular parallax image) photographed from two viewpoints to be stereoscopically viewed by using a special instrument such as eyeglasses for stereoscopic viewing. In recent years, monitors are also in practical use that enable, by using a light beam controller such as a lenticular lens, a multi-parallax image (such as a nine-parallax image) photographed from a plurality of viewpoints to be stereoscopically viewed by naked eyes. There are also cases in which depth information of an image photographed from one viewpoint is estimated, and the estimate information is used in image processing to generate the two-parallax image or the nine-parallax image to be displayed on the stereoscopically viewable monitor.

As medical image diagnostic apparatuses, such as an X-ray computed tomography (CT) apparatus, a magnetic resonance imaging (MRI) apparatus, and an ultrasonic diagnostic apparatus, there are practically used apparatuses that can generate three-dimensional medical image data (volume data). Conventionally, the volume data generated by such a medical image diagnostic apparatus is subjected to various types of image processing (rendering processing) to be provided as a two-dimensional image (rendering image), and two-dimensionally displayed on a general-purpose monitor. For example, the volume data generated by the medical image diagnostic apparatus is provided by volume rendering as a two-dimensional image (volume rendering image) reflecting three-dimensional information, and two-dimensionally displayed on the general-purpose monitor.

Here, there have been cases in which troublesome setting is needed to make the stereoscopically viewable monitor display a medical image suitable for image interpretation because there are various display methods to make the stereoscopically viewable monitor display the medical image. For example, there has been a case in which troublesome setting is needed to set, for example, how much stereoscopic effect is to be given to an image to be displayed and from what angle the image is to be displayed.

BRIEF DESCRIPTION OF THE DRAWINGS

FIG. 17 is a chart illustrating an example of setting information stored by a memory according to the third embodiment;

DETAILED DESCRIPTION

According to an embodiment, a medical image diagnostic apparatus includes an accepting unit, an extracting unit and a setting unit. The accepting unit configured to accept input of conditions with respect to regions to be photographed and arrangement of the regions. The extracting unit configured to extract an area of interest of each subject by analyzing medical image data photographed based on the conditions accepted by the accepting unit. The setting unit configured to set display conditions of a parallax image group to be displayed on a display unit having a stereoscopic viewing function, based on the conditions and on the area of interest extracted by the extracting unit.

Embodiments of a medical image diagnostic apparatus, a medical image processing apparatus, and methods therefor will be described below in detail with reference to the accompanying drawings. The description will be made below of an example in which an X-ray CT apparatus is exemplified as the medical image diagnostic apparatus. First of all, terms to be used in the embodiments below are explained as follows. The term "parallax image group" refers to an image group that is generated by applying volume rendering processing to volume data while moving a viewpoint position in increments of a predetermined parallax angle. That is, the "parallax image group" is constituted by a plurality of "parallax images" whose "viewpoint positions" differ from each other. The term "parallax angle" refers to an angle determined by adjacent viewpoint positions among the viewpoint positions set for generating the "parallax image group" and a predetermined position in a space (such as the center of the space) represented by the volume data. The term "number of parallaxes" refers to the number of "parallax images" required for being stereoscopically viewed on a stereoscopic display monitor. The term "nine-parallax image" to be described later refers to the "parallax image group" constituted by nine "parallax images". The term "two-parallax image" to be described later refers to the "parallax image group" constituted by two "parallax images".

First Embodiment

The X-ray CT apparatus is an apparatus that irradiates a subject with X-rays from an X-ray tube, then detects the X-rays transmitted through the subject with a detector, and thereby reconstructs an X-ray CT image representing morphological information of tissue in the subject. In addition to reconstructing the X-ray CT image, the X-ray CT apparatus according to a first embodiment calculates a "degree of infiltration" that indicates a degree to which a tumor infiltrates in surrounding regions, such as peripheries, of lungs.

Figure 1:
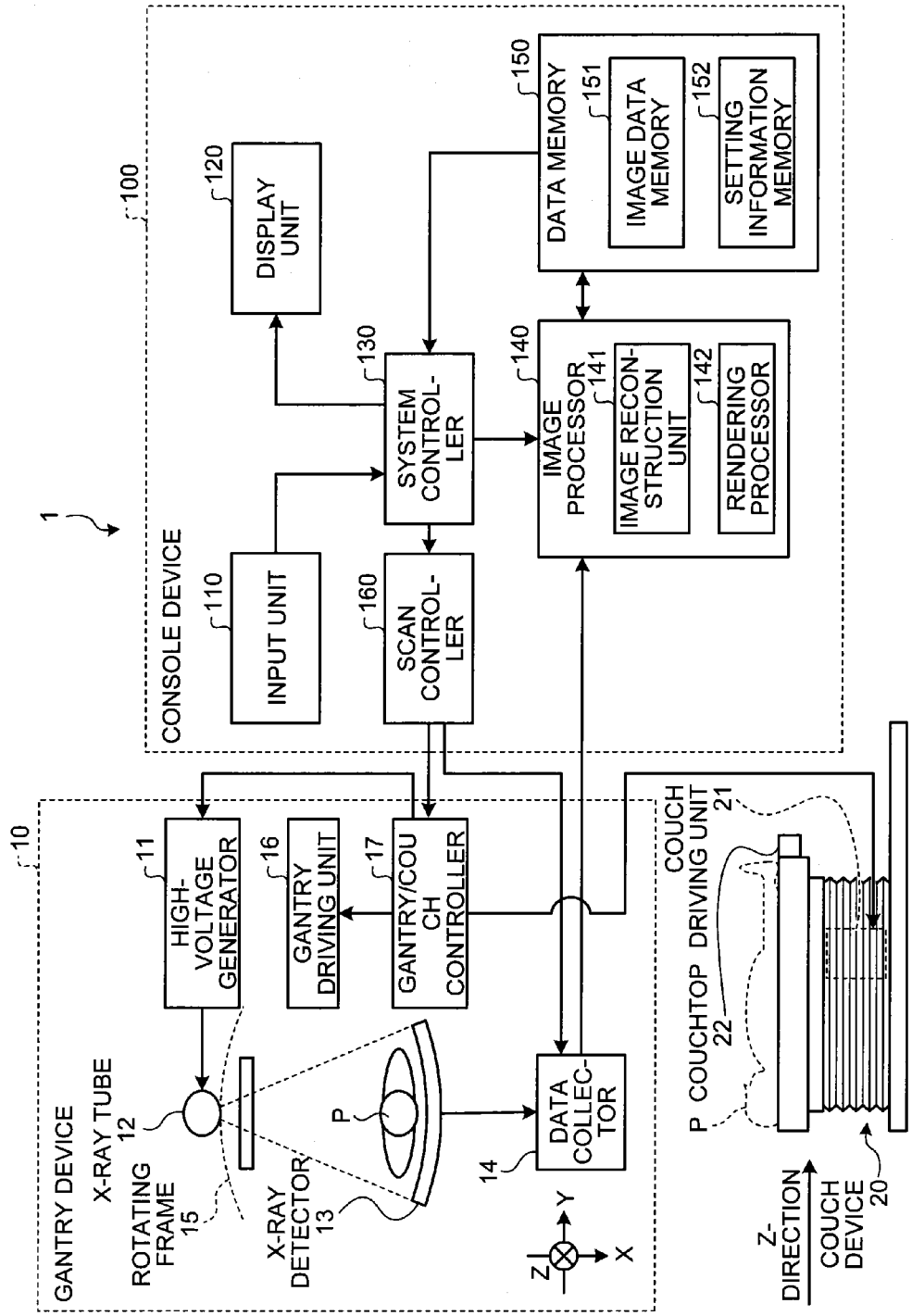
FIG. 1 is a diagram illustrating a configuration example of an X-ray CT apparatus according to a first embodiment.

A configuration of the X-ray CT apparatus according to the first embodiment will be described using FIG. 1. FIG. 1 is a diagram illustrating a configuration example of this X-ray CT apparatus 1 according to the first embodiment. As illustrated in FIG. 1, the X-ray CT apparatus 1 according to the first embodiment includes a gantry device 10, a couch device 20, and a console device 100.

The gantry device 10 irradiates a subject P with X-rays, then detects the X-rays transmitted through the subject P, and outputs the detected X-rays to the console device 100. The gantry device 10 such as described above includes a high-voltage generator 11, an X-ray tube 12, an X-ray detector 13, a data collector 14, a rotating frame 15, a gantry driving unit 16, and a gantry/couch controller 17.

The high-voltage generator 11 supplies a high voltage to the X-ray tube 12 according to control by the gantry/couch controller 17. The X-ray tube 12 is a vacuum tube that generates X-rays with the high voltage supplied from the high-voltage generator 11, and irradiates the subject P with the X-rays along with rotation of the rotating frame 15. More specifically, the high-voltage generator 11 adjusts the tube voltage and the tube current supplied to the X-ray tube 12, and thereby adjusts the X-ray dosage incident on the subject P.

The X-ray detector 13 is a two-dimensional array detector (plane detector) that detects the X-rays transmitted through the subject P, and is arranged, along the direction of the body axis of the subject P (the Z-axis direction illustrated in FIG. 1), with a plurality of detection element rows disposed with a plurality of channels of X-ray detection elements. Specifically, the X-ray detector 13 in the first embodiment includes the X-ray detection elements arranged in multiple rows, such as 320 rows, along the direction of the body axis of the subject P, and thus can detect the X-rays transmitted through the subject P in a wide area, such as an area including the lungs and heart of the subject P.

The data collector 14 generates projection data by using the X-rays detected by the X-ray detector 13, and sends the generated projection data to an image processor 140 of the console device 100. The rotating frame 15 is a circular ring-like frame rotating in a high-speed and continuous manner around the subject P serving as a center of rotation, and includes the X-ray tube 12 and the X-ray detector 13 arranged in a manner opposed to each other.

The gantry driving unit 16 drives the gantry according to control by the gantry/couch controller 17. Specifically, the gantry driving unit 16 continuously rotates the rotating frame 15 at a high speed by driving it with a motor, and thus continuously rotates the X-ray tube 12 and the X-ray detector 13 in a circular orbit around the subject P serving as the center of rotation. The gantry/couch controller 17 controls the high-voltage generator 11, the gantry driving unit 16, and a couch driving unit 21 according to control by a scan controller 160 to be described later.

The couch device 20 is a bed on which the subject P to be photographed is placed, and includes the couch driving unit 21 and a couchtop 22. The couch driving unit 21 continuously reciprocates the couchtop 22 in the direction of the body axis of the subject P by driving the couchtop 22 with a motor according to control by the gantry/couch controller 17. The couchtop 22 is a plate on which the subject P is placed.

In an inspection using the X-ray CT apparatus 1, the couchtop 22 is moved while the X-rays are emitted from the X-ray tube 12 in a fixed state of the rotating frame 15, and thereby, a scanogram is taken by scanning the entire body of the subject P along the direction of the body axis thereof. Then, an operator who has referred to the scanogram of the subject P makes a plan for photographing the X-ray CT image. Hereby, the gantry device 10 performs, for example, a helical scan in which the rotating frame 15 is rotated while the couchtop 22 is moved so as to scan the subject P in a spiral manner. Alternatively, the gantry device 10 performs a conventional scan in which the couchtop 22 is moved, and thereafter, the rotating frame 15 is rotated while the subject P is fixed in position so as to scan the subject P along a circular orbit.

As illustrated in FIG. 1, the console device 100 includes an input unit 110, a display unit 120, a system controller 130, the image processor 140, a data memory 150, and the scan controller 160. The console device 100 accepts operation of the X-ray CT apparatus 1 by the operator, and reconstructs an X-ray CT image from the projection data collected by the gantry device 10. The console device 100 then generates a parallax image group from the X-ray CT image, and displays the parallax image group on a stereoscopically viewable monitor. Note that the parallax image group refers to a plurality of parallax images whose viewpoint positions differ from each other.

The input unit 110 includes, for example, a mouse and a keyboard used by the operator of the X-ray CT apparatus 1 for entering various instructions and various settings, and transfers the information on the instructions and the settings accepted from the operator to the system controller 130. The input unit 110 accepts from the operator, for example, operation regarding setting of a scanning plan and a reconstruction plan, and editing operation regarding various settings in the case of displaying medical images on a 3D monitor. In the setting operation of the scanning plan, the X-ray CT apparatus 1 can also allow the operator to select an optimal scanning plan from scanning plans in which various conditions are set in advance according to attribute information (such as sex, age, and physique) of the subject, the purpose of inspection, regions to be inspected, and so on. The scanning plan set in advance in this manner is called an "expert plan (EP)".

The display unit 120 is a stereoscopically viewable monitor (hereinafter called a stereoscopic display monitor), and displays various types of information. The display unit 120 displays, for example, the parallax image group generated from the X-ray CT image stored by the data memory 150 and graphical user interfaces (GUIs) for accepting various instructions from the operator.

Here, the stereoscopic display monitor will be described. An ordinary general-purpose monitor that is currently most commonly used displays two-dimensional images in two dimensions, and cannot display the two-dimensional images stereoscopically. If an observer desires stereoscopic viewing on the general-purpose monitor, an apparatus that outputs the image to the general-purpose monitor needs to use a parallel method or an intersection method to display, in a parallel manner, two parallax images that are stereoscopically viewable by the observer. Alternatively, the apparatus that outputs the image to the general-purpose monitor needs to display images that are stereoscopically viewable by the observer with a complementary color method, for example, by using eyeglasses that have a red cellophane film attached to a portion for the left eye and a blue cellophane film attached to a portion for the right eye.

On the other hand, as the stereoscopic display monitor, there is a monitor that enables the two-parallax image (also called "binocular parallax image") to be stereoscopically viewed by using a special instrument such as eyeglasses for stereoscopic viewing.

Figure 2A:
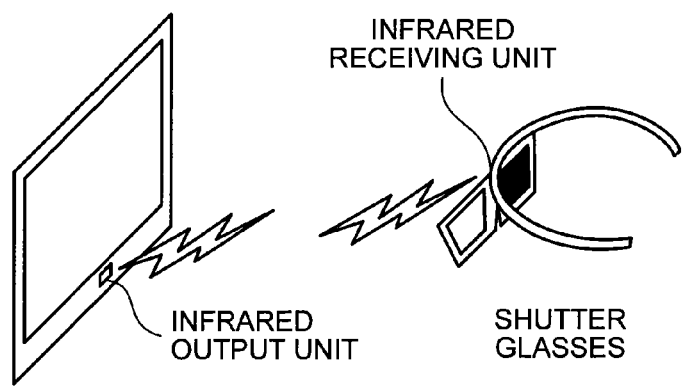
FIG. 2A is a view for explaining an example of a stereoscopic display monitor that performs stereoscopic display by using a two-parallax image.
Figure 2B:
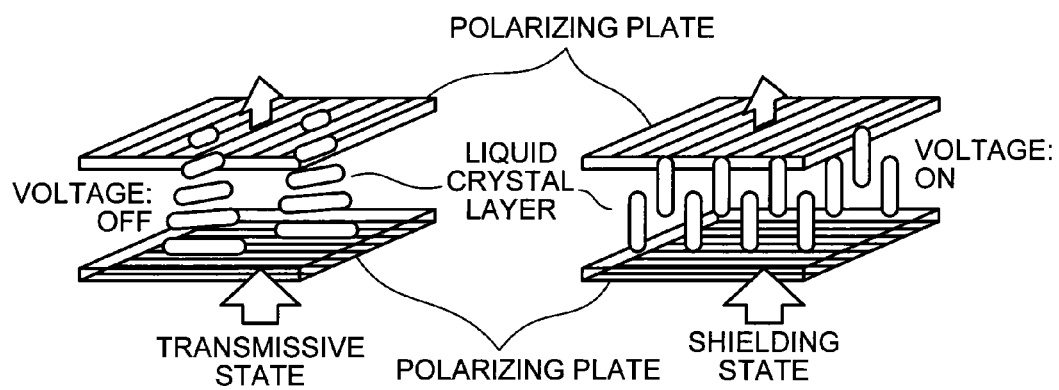
FIG. 2B is a view for explaining the example of the stereoscopic display monitor that performs the stereoscopic display by using the two-parallax image.

FIGS. 2A and 2B are views for explaining an example of the stereoscopic display monitor that performs stereoscopic display by using the two-parallax image. The example illustrated in FIGS. 2A and 2B is a stereoscopic display monitor that performs the stereoscopic display by using a shutter method, in which shutter glasses are used as the eyeglasses for stereoscopic viewing worn by the observer who observes the monitor. Such a stereoscopic display monitor alternately outputs two parallax images on the monitor. For example, the monitor illustrated in FIG. 2A alternately outputs an image for the left eye and an image for the right eye at 120 Hz. Here, as illustrated in FIG. 2A, an infrared output unit is installed on the monitor, and controls output of an infrared ray in accordance with the timing of switching of the images.

The infrared ray that has exited from the infrared output unit is received by an infrared receiving unit of the shutter glasses illustrated in FIG. 2A. A shutter is mounted at each of right and left frames of the shutter glasses, which switches the right and left shutters alternately between a transmissive state and a shielding state in accordance with the timing of receiving of the infrared ray by the infrared receiving unit. The switching process between the transmissive state and the shielding state in the shutters will be described below.

As illustrated in FIG. 2B, each of the shutters has a polarizing plate on the incident side and a polarizing plate on the exit side, and also has a liquid crystal layer between the incident side polarizing plate and the exit side polarizing plate. The incident side polarizing plate and the exit side polarizing plate are perpendicular to each other as illustrated in FIG. 2B. Here, as illustrated in FIG. 2B, in the state of OFF in which no voltage is applied, the light that has passed through the incident side polarizing plate is rotated by 90 degrees by an effect of the liquid crystal layer, and then, passes through the exit side polarizing plate. In other words, the shutter to which no voltage is applied is placed in the transmissive state.

On the other hand, as illustrated in FIG. 2B, in the state of ON in which a voltage is applied, the light that has passed through the incident side polarizing plate is shielded by the exit side polarizing plate because a polarization rotation effect by liquid crystal molecules in the liquid crystal layer disappears. In other words, the shutter to which a voltage is applied is placed in the shielding state.

Accordingly, the infrared output unit, for example, outputs the infrared ray during a period while the image for the left eye is displayed on the monitor. Then, during the period while receiving the infrared ray, the infrared receiving unit applies a voltage to the shutter for the right eye without applying a voltage to the shutter for the left eye. With this operation, as illustrated in FIG. 2A, the image for the left eye enters the observer's left eye because the shutter for the right eye is placed in the shielding state while the shutter for the left eye is placed in the transmissive state. On the other hand, the infrared output unit stops outputting the infrared ray during a period while the image for the right eye is displayed on the monitor. Then, during the period while not receiving the infrared ray, the infrared receiving unit applies a voltage to the shutter for the left eye without applying a voltage to the shutter for the right eye. With this operation, the image for the right eye enters the observer's right eye because the shutter for the left eye is placed in the shielding state while the shutter for the right eye is placed in the transmissive state. In this manner, the stereoscopic display monitor illustrated in FIGS. 2A and 2B displays the images that are stereoscopically viewable by the observer by switching the images and the states of the shutters in conjunction with each other. Note that, as the stereoscopic display monitor that enables the two-parallax image to be stereoscopically viewed, there is also known, in addition to the monitor employing the shutter method described above, a monitor that employs a polarized glasses method.

Moreover, as a stereoscopic display monitor that has been brought into practical use in recent years, there is a monitor that enables a multi-parallax image, such as the nine-parallax image, to be stereoscopically viewed by the observer with naked eyes by using a light beam controller such as a lenticular lens. Such a stereoscopic display monitor enables stereoscopic viewing by binocular parallax, and further enables stereoscopic viewing by motion parallax in which an observed video image changes in accordance with movement of viewpoint of the observer.

Figure 3:
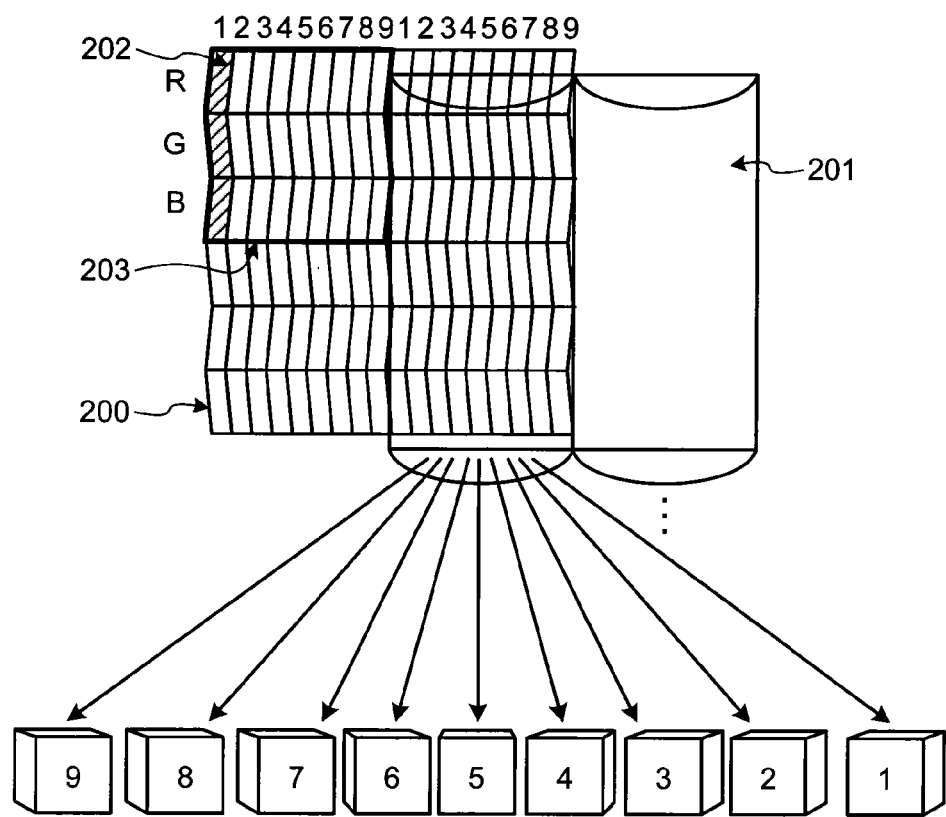
FIG. 3 is a diagram for explaining an example of a stereoscopic display monitor that performs stereoscopic display by using a nine-parallax image.

FIG. 3 is a diagram for explaining an example of the stereoscopic display monitor that performs the stereoscopic display by using the nine-parallax image. The stereoscopic display monitor illustrated in FIG. 3 is arranged with the light beam controller on the front surface a flat display surface 200 such as a liquid crystal panel. For example, in the stereoscopic display monitor illustrated in FIG. 3, a vertical lenticular sheet 201 with optical apertures extending in the vertical direction is stuck as the light beam controller on the front surface the flat display surface 200. In the example illustrated in FIG. 3, the vertical lenticular sheet 201 is stuck so that convex parts thereof serve as a front surface. However, the example may be a case in which the vertical lenticular sheet 201 is stuck so that the convex parts thereof face the display surface 200.

As illustrated in FIG. 3, the display surface 200 is arranged in a matrix configuration with pixels 202, each of which has an aspect ratio of 3 to 1 and is arranged in the vertical direction with three subpixels of red (R), green (G), and blue (B). The stereoscopic display monitor illustrated in FIG. 3 converts the nine-parallax image constituted by nine images into an intermediate image in which the nine images are arranged in a predetermined format (such as a grid pattern), and then, outputs the intermediate image to the display surface 200. In other words, the stereoscopic display monitor illustrated in FIG. 3 allocates nine pixels located in the same position in the nine-parallax image to respective nine columns of the pixels 202, and outputs the nine columns. The nine columns of the pixels 202 form a unit pixel group 203 that simultaneously displays nine images whose viewpoint positions differ from each other.

The nine-parallax image that is simultaneously output as the unit pixel group 203 on the display surface 200 is emitted as parallel light, for example, by a light-emitting diode (LED) backlight, and further, radiated in multiple directions by the vertical lenticular sheet 201. Because the light of the pixels of the nine-parallax image is radiated in multiple directions, the light entering the right eye and the left eye of the observer changes in conjunction with the position (position of viewpoint) of the observer. That is, the parallax image entering the right eye and the parallax image entering the left eye have different parallax angles from each other depending on the angle of view of the observer. For this reason, the observer can stereoscopically view a photographed object, for example, in each of the nine positions illustrated in FIG. 3. Further, for example, the observer can stereoscopically view, in the position 5 illustrated in FIG. 3, the photographed object in the state of directly facing the photographed object, and in addition, can stereoscopically view, in each position other than the position 5 illustrated in FIG. 3, the photographed object in the state in which the direction of the photographed object is changed. Note that the stereoscopic display monitor illustrated in FIG. 3 is merely an example. There may be a case in which the stereoscopic display monitor displaying the nine-parallax image is, as illustrated in FIG. 3, a horizontal stripe liquid crystal display arranged as "RRR . . . , GGG . . . , BBB . . . " or a vertical stripe liquid crystal display arranged as "RGBRGB . . . ". In addition, there may be a case in which the stereoscopic display monitor illustrated in FIG. 3 is, as illustrated in FIG. 3, a vertical lens type in which the lenticular sheet is vertical or a slanted lens type in which the lenticular sheet is slanted.

Referring back to FIG. 1, the system controller 130 controls the entire X-ray CT apparatus 1 by controlling the gantry device 10, the couch device 20, and the console device 100. The system controller 130 controls, for example, the scan controller 160 to make it collect three-dimensional projection data. The system controller 130 also controls, for example, the image processor 140 to make it reconstruct an X-ray CT image from the three-dimensional projection data, and further to make it generate a parallax image group from the X-ray CT image. Furthermore, the system controller 130 displays the parallax image group generated by the image processor 140 on the display unit 120. Detailed processing of the system controller 130 will be described later in detail.

The image processor 140 includes an image reconstruction unit 141 and a rendering processor 142 as illustrated in FIG. 1. The image reconstruction unit 141 applies various types of processing to the three-dimensional projection data received from the data collector 14. Specifically, the image reconstruction unit 141 applies preprocessing such as sensitivity correction to the three-dimensional projection data received from the data collector 14, and then applies back projection processing to the preprocessed three-dimensional projection data, thereby reconstructing a three-dimensional X-ray CT image (hereinafter mentioned as "volume data"). Then, the image reconstruction unit 141 stores the reconstructed volume data in the data memory 150. For example, the image reconstruction unit 141 reconstructs, from the projection data collected by photographing the subject, medical image data of a plurality of axial planes along the direction of body axis of the subject, and thereby generates volume data. The image reconstruction unit 141 reconstructs, for example, medical image data of 500 axial planes. This group of the medical image data of 500 axial planes serves as the volume data. The data itself, such as the projection data or MR signals, of the subject photographed by the medical image diagnostic apparatus 310 may also serve as the volume data.

Under the control of the system controller 130, the rendering processor 142 applies various types of rendering processing to the volume data generated by the image reconstruction unit 141, and thus generates a parallax image group. Specifically, the rendering processor 142 according to the first embodiment reads the volume data from the data memory 150, and, first of all, preprocesses the volume data. Next, the rendering processor 142 applies the volume rendering processing to the preprocessed volume data, and thus generates a parallax image group.

Subsequently, the rendering processor 142 generates a two-dimensional image in which various types of information (such as scale marks, a patient name, and inspection items) are represented, and superimposes the generated two-dimensional image on each image in the parallax image group to generate two-dimensional images for output. Then, the rendering processor 142 stores the parallax image group and the two-dimensional images for output thus generated in the data memory 150. In the first embodiment, the rendering processing refers to the whole of image processing applied to the volume data, and the volume rendering processing refers to, in the rendering processing, the processing for generating the two-dimensional images reflecting three-dimensional information. For example, a parallax image corresponds to the medical image generated by the rendering processing. Details of the rendering processor 142 will be described later.

The data memory 150 includes an image data memory 151 and a setting information memory 152. The image data memory 151 stores therein, for example, the volume data reconstructed by the image reconstruction unit 141 and the parallax image group generated by the rendering processor 142. The setting information memory 152 stores therein setting information that serves as information regarding the generation of the parallax image group and that is used by the system controller 130 to be described later. The setting information will be described later in detail. The scan controller 160 controls the gantry/couch controller 17 based on scanning conditions instructed from the system controller 130.

Figure 4:
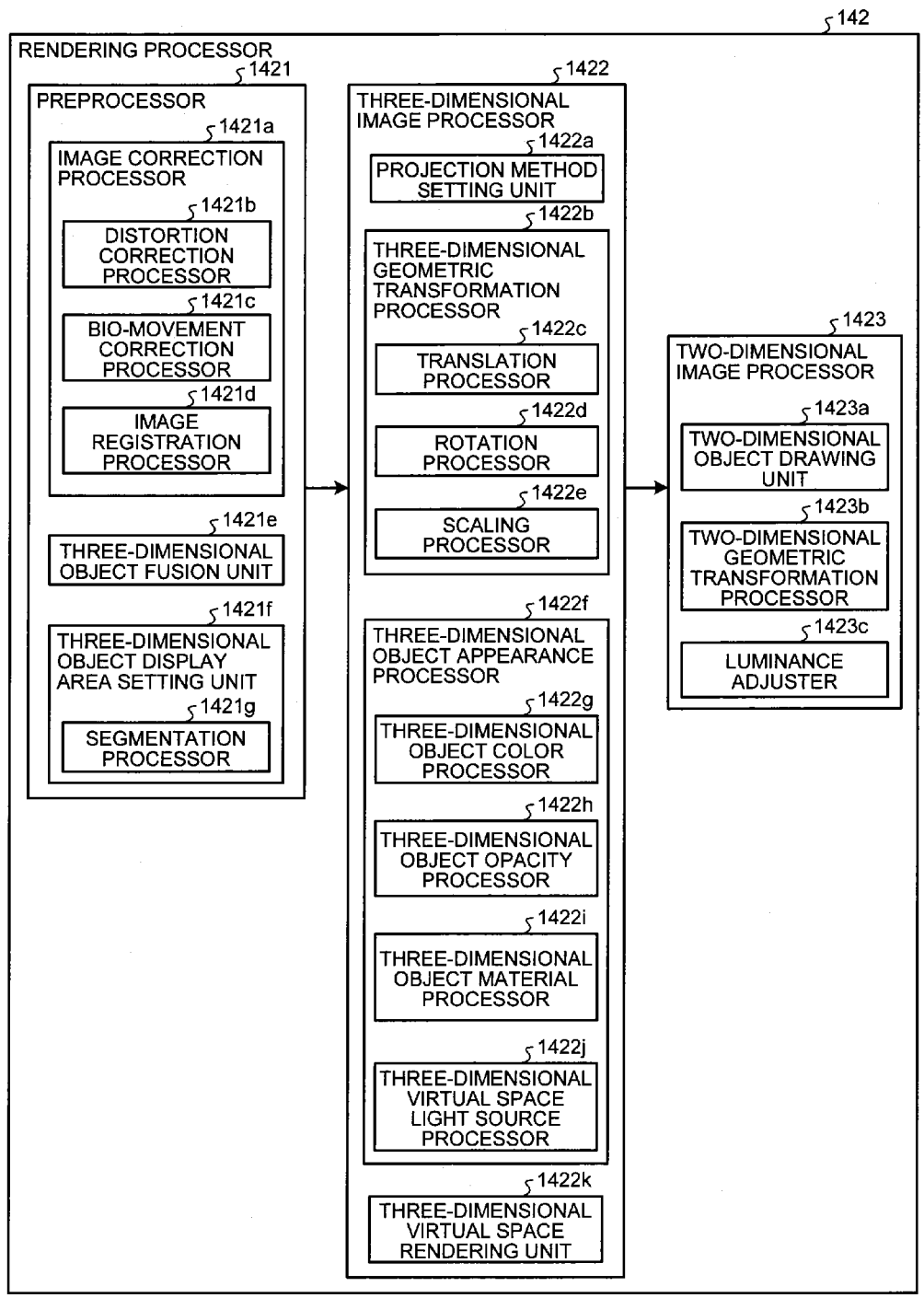
FIG. 4 is a diagram for explaining a configuration example of a rendering processor illustrated in FIG. 1.

Here, details of the rendering processor 142 will be described. FIG. 4 is a diagram for explaining a configuration example of the rendering processor 142 illustrated in FIG. 1. As illustrated in FIG. 4, the rendering processor 142 includes a preprocessor 1421, a three-dimensional image processor 1422, and a two-dimensional image processor 1423. The preprocessor 1421 preprocesses the volume data. The three-dimensional image processor 1422 generates a parallax image group from the preprocessed volume data. The two-dimensional image processor 1423 generates two-dimensional images for output constituting the parallax image group with the various types of information superimposed thereon. The processors will be described below in sequence.

The preprocessor 1421 is a processor that applies various types of preprocessing to the volume data before being subjected to the rendering processing, and includes an image correction processor 1421a, a three-dimensional object fusion unit 1421e, and a three-dimensional object display area setting unit 1421f.

The image correction processor 1421a is a processor that performs image correction processing when two types of volume data are processed as one piece of volume data, and, as illustrated in FIG. 4, includes a distortion correction processor 1421b, a bio-movement correction processor 1421c, and an image registration processor 1421d.

The distortion correction processor 1421b corrects distortion of data in each individual piece of the volume data caused by collection conditions at the time of data collection. The bio-movement correction processor 1421c corrects a movement caused by subject's body movement occurring at the time when pieces of data used for generating the individual piece of volume data are collected. The image registration processor 1421d performs position alignment (registration) between two pieces of volume data that have been subjected to the correction processes by the distortion correction processor 1421b and the bio-movement correction processor 1421c, for example, by using a cross-correlation method.

The three-dimensional object fusion unit 1421e fuses a plurality of pieces of volume data whose positions are aligned by the image registration processor 1421d. Note that the processes of the image correction processor 1421a and the three-dimensional object fusion unit 1421e are omitted when the rendering processing is applied to a single piece of volume data.

The three-dimensional object display area setting unit 1421f is a processor that sets a display area corresponding to a region to be displayed specified by the operator, and includes a segmentation processor 1421g. The segmentation processor 1421g is a processor that extracts, for example, an organ such as a heart, a lung, or a blood vessel, or a bone structure specified by the operator, for example, by using a region growing method based on pixel values (voxel values) of the volume data.

The segmentation processor 1421g does not perform segmentation processing if the operator has not specified any region to be displayed. If the operator has specified a plurality of regions to be displayed, the segmentation processor 1421g extracts the specified multiple regions. The processing of the segmentation processor 1421g may be executed again by a request for fine adjustment from the operator who has referred to the rendering image.

The three-dimensional image processor 1422 applies the volume rendering processing to the volume data preprocessed by the preprocessor 1421. As a processor performing the volume rendering processing, the three-dimensional image processor 1422 includes a projection method setting unit 1422a, a three-dimensional geometric transformation processor 1422b, a three-dimensional object appearance processor 1422f, and a three-dimensional virtual space rendering unit 1422k.

The projection method setting unit 1422a determines a projection method for generating the parallax image group. For example, the projection method setting unit 1422a determines whether the volume rendering processing is to be executed by a parallel projection method or a perspective projection method.

The three-dimensional geometric transformation processor 1422b is a processor that determines information for three-dimensional geometric transformation of the volume data to be subjected to the volume rendering processing, and includes a translation processor 1422c, a rotation processor 1422d, and a scaling processor 1422e. The translation processor 1422c is a processor that determines an amount of movement by which the volume data is to be translated if a viewpoint position when the volume rendering processing is performed is translated. The rotation processor 1422d is a processor that determines an amount of movement by which the volume data is to be rotationally moved if a viewpoint position when the volume rendering processing is performed is rotationally moved. The scaling processor 1422e is a processor that determines an enlargement ratio or a contraction ratio of the volume data when enlargement or contraction of the parallax image group is requested.

The three-dimensional object appearance processor 1422f includes a three-dimensional object color processor 1422g, a three-dimensional object opacity processor 1422h, a three-dimensional object material processor 1422i, and a three-dimensional virtual space light source processor 1422j. The three-dimensional object appearance processor 1422f uses these processors to perform processing to determine the display state of the displayed parallax image group, for example, based on the control by the system controller 130 to be described later.

The three-dimensional object color processor 1422g is a processor that determines a color in which each segmented area in the volume data is to be colored. The three-dimensional object opacity processor 1422h is a processor that determines opacity of voxels constituting each segmented area in the volume data. Note that, in the volume data, an area behind the area in which the opacity is set to 100% is not represented in the parallax image group. Note also that, in the volume data, an area in which the opacity is set to 0% is not represented in the parallax image group.

The three-dimensional object material processor 1422i is a processor that determines material of each segmented area in the volume data so as to adjust texture of the area when represented. The three-dimensional virtual space light source processor 1422j is a processor that determines the position and the type of a virtual light source placed in a three-dimensional virtual space when the volume rendering processing is applied to the volume data. The type of the virtual light source includes, for example, a light source that emits parallel light beams from an infinite distance and a light source that emits radial light beams from a viewpoint.

The three-dimensional virtual space rendering unit 1422k applies the volume rendering processing to the volume data, and thus generates a parallax image group. When applying the volume rendering processing, the three-dimensional virtual space rendering unit 1422k uses, as necessary, various types of information determined by the projection method setting unit 1422a, the three-dimensional geometric transformation processor 1422b, and the three-dimensional object appearance processor 1422f.

Here, the three-dimensional virtual space rendering unit 1422k applies the volume rendering processing in accordance with the rendering conditions. A rendering condition is, for example, "parallel projection method" or "perspective projection method". Another rendering condition is, for example, "standard viewpoint position and parallax angle". Further another rendering condition is, for example, "translation of viewpoint position", "rotational movement of viewpoint position", "enlargement of parallax image group", or "contraction of parallax image group". Still another rendering condition is, for example, "color used for coloring", "opacity", "texture", "position of virtual light source", or "type of virtual light source".

The rendering conditions such as mentioned above are accepted from the operator via the input unit 110, or initialized, or otherwise determined by the system controller 130 to be described later. In any case, the three-dimensional virtual space rendering unit 1422k accepts the rendering conditions from the system controller 130, and applies the volume rendering processing to the volume data in accordance with the rendering conditions. At this time, the projection method setting unit 1422a, the three-dimensional geometric transformation processor 1422b, and the three-dimensional object appearance processor 1422f determine various types of necessary information in accordance with the rendering conditions. Accordingly, the three-dimensional virtual space rendering unit 1422k uses the various types of information thus determined to generate a parallax image group.

Figure 5:
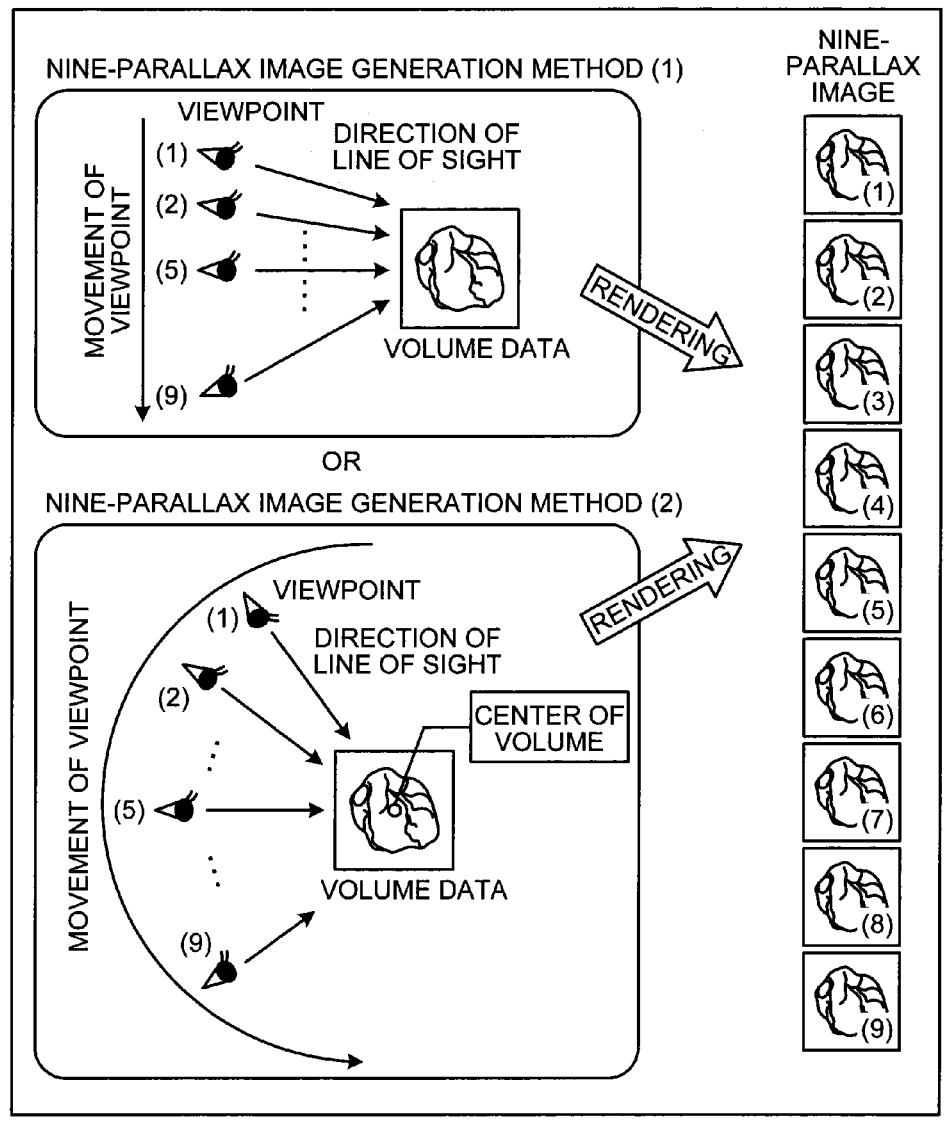
FIG. 5 is a diagram for explaining an example of volume rendering processing according to the first embodiment.

FIG. 5 is a diagram for explaining an example of the volume rendering processing according to the first embodiment. For example, it is assumed that, as illustrated in Nine-Parallax Image Generation Method (1) of FIG. 5, the three-dimensional virtual space rendering unit 1422k accepts the parallel projection method, and further accepts a standard viewpoint position (5) and a parallax angle of one degree as rendering conditions. In such a case, the three-dimensional virtual space rendering unit 1422k translates the positions of the viewpoints from (1) to (9) so that the parallax angle (angle between directions of lines of sight) is changed at intervals of one degree, and thus, generates nine parallax images having parallax angles changed at the intervals of one degree by using the parallel projection method. When using the parallel projection method, the three-dimensional virtual space rendering unit 1422k sets a light source that emits parallel light beams from an infinite distance along a line of sight.

Alternatively, it is assumed that, as illustrated in Nine-Parallax Image Generation Method (2) of FIG. 5, the three-dimensional virtual space rendering unit 1422k accepts the perspective projection method, and further accepts the standard viewpoint position (5) and the parallax angle of one degree as rendering conditions. In such a case, the three-dimensional virtual space rendering unit 1422k rotationally moves the positions of the viewpoints from (1) to (9) so that the parallax angle is changed at intervals of one degree about the center (centroid) of the volume data, and thus, generates nine parallax images having parallax angles changed at the intervals of one degree by using the perspective projection method. When using the perspective projection method, the three-dimensional virtual space rendering unit 1422k sets, at each viewpoint, a point light source or a surface light source that radially emits light in a three-dimensional manner from the center in the directions of lines of sight. Depending on the rendering conditions, the perspective projection method may be used in the case in which the viewpoints (1) to (9) are arranged by translation. The lines of sight are directed from the viewpoints to the center (centroid) of a sectional plane of the volume data as illustrated in FIG. 5.

The three-dimensional virtual space rendering unit 1422k may perform the volume rendering processing using a combination of the parallel projection method and the perspective projection method by setting a light source that radially emits light in a two-dimensional manner from the center in the directions of lines of sight with respect to the vertical direction of the displayed volume rendering image and that emits parallel light beams from an infinite distance along a line of sight with respect to the horizontal direction of the displayed volume rendering image.

The three-dimensional virtual space rendering unit 1422k also has, in addition to the volume rendering function, a function to reconstruct an MPR image from the volume data by using a multiplanar reconstruction (MPR) method. The three-dimensional virtual space rendering unit 1422k also has a function to perform curved MPR as the MPR and a function to perform intensity projection.

The parallax image group generated from the volume data by the three-dimensional image processor 1422 is used as underlays. Then, the overlay in which the various types of information (such as scale marks, a patient name, and inspection items) are represented is superimposed on the underlays so as to form two-dimensional images for output. The two-dimensional image processor 1423 is a processor that generates two-dimensional images for output by applying image processing to the overlay and the underlays, and, as illustrated in FIG. 4, includes a two-dimensional object drawing unit 1423a, a two-dimensional geometric transformation processor 1423b, and a luminance adjuster 1423c. For example, in order to reduce a load required for the generation processing of the two-dimensional images for output, the two-dimensional image processor 1423 superimposes one overlay on each of the nine respective parallax images (underlays) to generate nine two-dimensional images for output.

The two-dimensional object drawing unit 1423a is a processor that draws various types of information to be represented on the overlay. The two-dimensional geometric transformation processor 1423b is a processor that translates or rotationally moves positions of the various types of information to be represented on the overlay and that enlarges or contracts the various types of information to be represented on the overlay. The luminance adjuster 1423c is a processor that performs luminance conversion processing, and is a processor that adjusts luminance levels of the overlay and the underlays depending on parameters for image processing, such as the gradation, the window width (WW), and the window level (WL) of the stereoscopic display monitor that receives the output.

The parallax image group generated by the rendering processor 142 is stored in the data memory 150. Thereafter, for example, the X-ray CT apparatus 1 converts the parallax image group with the overlay image superimposed thereon into the intermediate image in which the parallax image group is arranged in the predetermined format (such as the grid pattern), and then, displays the intermediate image on the stereoscopic display monitor. Thus, medical doctors and inspection engineers as users can display the stereoscopic image in which the various types of information (such as scale marks, a patient name, and inspection items) are represented.

The overall configuration of the X-ray CT apparatus 1 according to the first embodiment has been described above. Under the configuration such as described above, the X-ray CT apparatus 1 according to the first embodiment is structured to be capable of easily displaying an optimal medical image for image interpretation on the monitor for stereoscopic viewing, using processing by the system controller 130 described below in detail.

Figure 6:
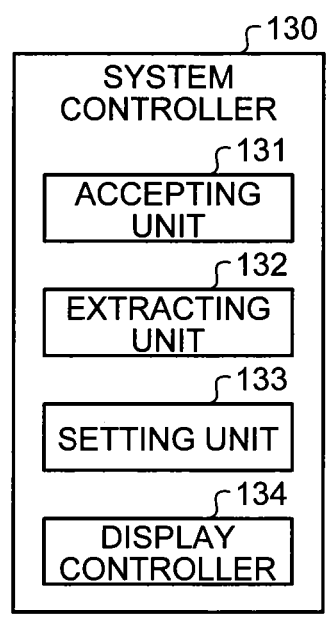
FIG. 6 is a diagram illustrating a configuration example of a system controller according to the first embodiment.

FIG. 6 is a diagram illustrating a configuration example of the system controller 130 according to the first embodiment. As illustrated in FIG. 6, the system controller 130 according to the first embodiment includes an accepting unit 131, an extracting unit 132, a setting unit 133, and a display controller 134.

The accepting unit 131 accepts input of conditions with respect to regions to be photographed and arrangement of the regions. Specifically, when the X-ray CT apparatus 1 executes diagnostic imaging, the accepting unit 131 accepts photographing conditions and reconstructing conditions entered from the operator via the input unit 110. The accepting unit 131 accepts, for example, information on the scanning plan and the reconstruction plan. To name some examples, the accepting unit 131 accepts information included in the scanning plan, such as diagnosis regions (such as a heart, lungs, and bones) and use of a contrast agent, accepts reconstruction functions included in the reconstruction plan that are used for correction processing for the projection data, image processing, and reconstruction of the volume data, and accepts the reconstructing conditions for reconstructing the volume data, including directions and sequences with respect to organs and bone structures.

The extracting unit 132 extracts an area of interest of each subject by analyzing the medical image data photographed based on the conditions accepted by the accepting unit 131. Specifically, the extracting unit 132 extracts an area of interest by analyzing the volume data generated based on the photographing conditions and the reconstructing conditions accepted by the accepting unit 131. More specifically, the extracting unit 132 extracts an area of interest such as a blood vessel region or a lesioned region by using the volume data stored by the image data memory 151. For example, the extracting unit 132 uses a threshold method or the region growing method to extract, for example, a mediastinum (trachea and bronchi) or a blood vessel, or uses a computer assisted diagnosis (CAD) to extract a lesioned region. As an example, description will be made of a case of extracting a lesioned region of a lung when chest X-ray CT photographing is performed using a multi-slice CT.

Here, in the following example, description will be made of a case of extracting a lung nodule as the lesioned region. In general, existence of a large nodule, an irregular edge (such as a protrusion, a pleural indentation, or a crack), or a vasa vasorum suggests a malignant nodule while a smooth edge, uniform density, or calcification suggests a benign nodule. For example, when extracting the lesioned region using the CAD, the extracting unit 132 reads out the volume data stored by the image data memory 151, and then extracts, based on a CT value, the lung nodule from the volume data thus read out. Specifically, the extracting unit 132 extracts an area having a relatively large CT value as the lung nodule. The CT value is known to be greater in the lung nodule than in the lung parenchyma, and thus, the lung nodule and the lung parenchyma can be distinguished by using the CT value. Note that other areas, such as ribs, having a large CT value can be excluded by using a lung mask.

Figure 7A:
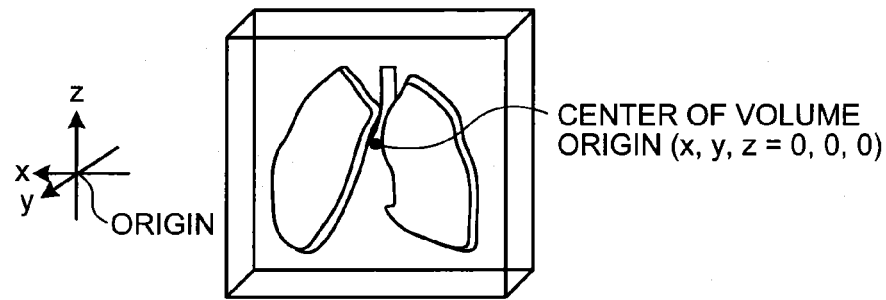
FIGS. 7A to 7C are diagrams for explaining an example of processing by an extracting unit according to the first embodiment.
Figure 7B:
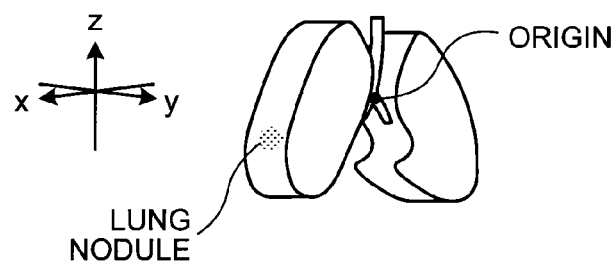
Figure 7C:
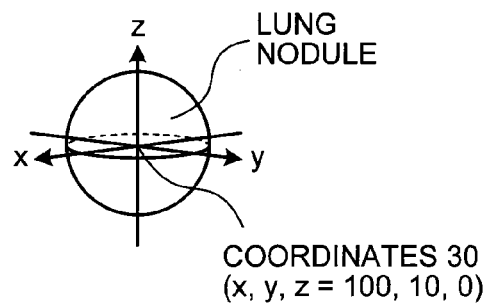

Then, the extracting unit 132 sets a Cartesian coordinate system consisting of three axes (x-axis, y-axis, and z-axis) having an origin at the center of volume (or centroid), and calculates coordinates of the extracted lung nodule in the Cartesian coordinate system thus set. FIGS. 7A to 7C are diagrams for explaining an example of processing by the extracting unit 132 according to the first embodiment. For example, the extracting unit 132 sets a coordinate system of three axes having an origin (x, y, z=0, 0, 0) at the center of volume, as illustrated in FIG. 7A. Then, the extracting unit 132 extracts the lung nodule illustrated in FIG. 7B based on the CT value, and calculates the coordinates of the extracted lung nodule.

Here, the extracting unit 132 calculates, as the coordinates of the lung nodule, for example, coordinates of the centroid of the lung nodule, or coordinates of the center of the smallest cube including the coordinates of the maximum values and the coordinates of the minimum values on the three axes. For example, as illustrated in FIG. 7C, the extracting unit 132 calculates coordinates 30 (x, y, z=100, 10, 0) of the centroid of the lung nodule as the coordinates of the lung nodule.

In the example described above, the case has been described in which an area of interest is extracted using the CAD. However, the disclosed technology is not limited to this case. There may be a case in which, for example, an area of interest is extracted using an analysis application that obtains positional information of the heart, the lungs, and the blood vessels by using the volume data reconstructed by the image reconstruction unit 141. There may also be a case in which an area of interest is extracted based on patient information. In such a case, the accepting unit 131 accepts the patient information. That is, there may be a case of using any conditions as far as they are the conditions with respect to regions to be photographed and arrangement of the regions.

Referring back to FIG. 6, the setting unit 133 sets display conditions of the parallax image group to be displayed on the display unit having the stereoscopic viewing function, based on the conditions accepted by the accepting unit 131 and the area of interest extracted by the extracting unit 132. Specifically, the setting unit 133 sets the display conditions based on the photographing conditions and the reconstructing conditions accepted by the accepting unit 131 and on the area of interest extracted by the extracting unit 132. More specifically, the setting unit 133 sets, as the display conditions, at least one of a condition regarding the generation of the parallax image group and conditions regarding the display of the parallax image group. In detail, the setting unit 133 sets the parallax angle of the parallax image group as the condition for generating the parallax image group. On the other hand, the setting unit 133 sets the position and the display direction of an object to be displayed to be represented in the parallax image group as the conditions regarding the display of the parallax image group.

Figure 8:
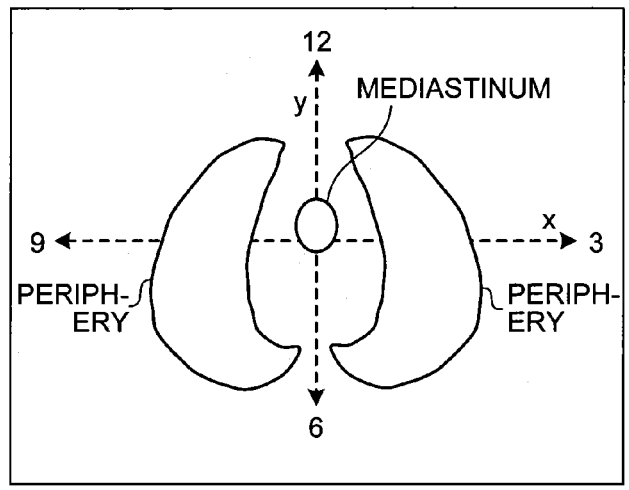
FIG. 8 is a diagram for explaining an example of processing of a setting unit according to the first embodiment.

For example, based on the photographing conditions, the setting unit 133 determines the structure of the object to be displayed included in the volume data, then determines the relative position of the region of interest extracted by the extracting unit 132 in the determined structure of the object to be displayed, and sets the display conditions so that the image including the determined relative position of the region of interest is displayed on the display unit 120. To take an example, based on conditions, such as a region to be scanned, the orientation (head-first or feet-first) of the patient's body when scanned, the direction of scanning (in or out), and the field of view (FOV), included in the photographing conditions, the setting unit 133 determines the structure of the diagnosis region in the volume data, then determines the relative position of the area of interest in the determined structure of the diagnosis region, and sets, for example, the viewpoints and the rotational angle relative to the area of interest. Description will be made using FIG. 8 of a case in which the lungs are selected as the region to be scanned, and the mediastinum and the peripheries are extracted as the area of interest. FIG. 8 is a diagram for explaining an example of processing of the setting unit 133 according to the first embodiment.

FIG. 8 illustrates the structure of the volume data when viewed from the direction of feet. For example, the setting unit 133 determines the state of placement of the lungs in the volume data based on the orientation of the patient's body when scanned, the direction of scanning, the FOV, and structural features of the lungs serving as the region to be scanned. That is, as illustrated in FIG. 8, the setting unit 133 determines that a position to observe the mediastinum is located in the direction of 12 o'clock on the y-axis, and the positions to observe the peripheral areas are located in the directions of 3 o'clock and 9 o'clock on the x-axis.

Figure 9A:
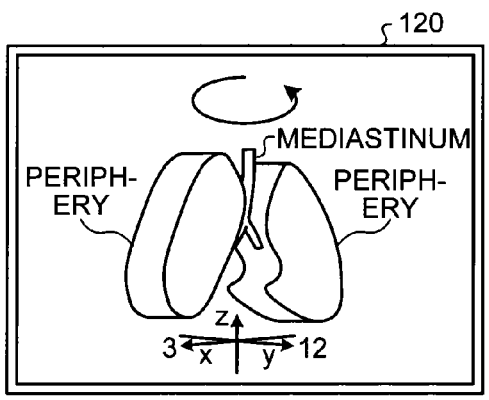
FIG. 9A is a view illustrating an example of an image displayed by a display unit according to the first embodiment.
Figure 9B:
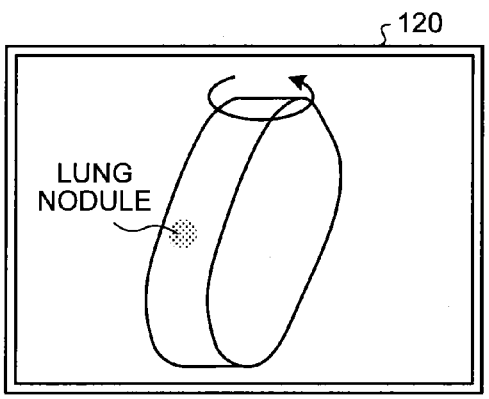
FIG. 9B is a view illustrating an example of an image displayed by the display unit according to the first embodiment.

Then, the setting unit 133 sets the display conditions so that the mediastinum and the peripheries serving as the area of interest are displayed on the display unit 120. FIGS. 9A and 9B are views each illustrating an example of an image displayed by the display unit according to the first embodiment. For example, as illustrated in FIG. 9A, the setting unit 133 sets the display conditions so as to display the whole of the image while rotating the image from left to right about the z-axis as a pivot.

Here, the setting unit 133 can set the display conditions for each of the mediastinum and the peripheries serving as the area of interest. For example, the setting unit 133 can set the display conditions so as to generate a parallax image group having a small parallax angle for the mediastinum area and a large parallax angle for the peripheral areas. With these settings, the setting unit 133 can display the image of the peripheral areas having an appearance of more depth than that of the mediastinum area, and thus can provide the image that is more suitable for image interpretation. In such a case, for example, the image illustrated in FIG. 9A is automatically switched to the parallax image group having a large parallax angle when the mediastinum area is rotated to come to the front of the display unit.

On the other hand, if, for example, the lung nodule illustrated in FIGS. 7A to 7C is the area of interest, the setting unit 133 determines the position of the coordinates 30 (x, y, z=100, 10, 0) of the lung nodule calculated by the extracting unit 132 relative to the structure of the lungs in the volume data. Then, as illustrated in FIG. 9B, the setting unit 133 sets the display conditions so that the lung nodule located in the right peripheral area is displayed in the center of the display unit 120.

In the case of rotating the stereoscopically viewable three-dimensional image as described above, for example, the rendering processor 142 changes the direction of line of sight with respect to the volume data in small steps, and at each step, performs the rendering processing as many times as the number of parallaxes to generate a plurality of parallax image groups, and the rendering processor 142 displays the generated parallax image groups on the display unit 120 in the order of the generation.

Figures 10, 11:
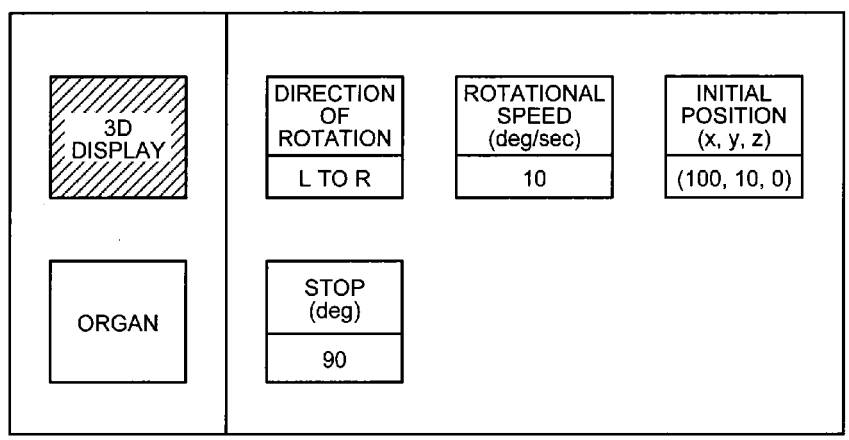
FIG. 10 is a chart illustrating an example of setting information stored by a setting information memory according to the first embodiment.
FIG. 11 is a diagram for explaining an example of processing by a display controller according to the first embodiment.

As described above, the setting unit 133 automatically sets the display conditions based on the photographing conditions and the area of interest. However, the setting unit 133 according to the first embodiment can set the display conditions of the parallax image group to be displayed on the display unit 120 by referring to the setting information stored by the setting information memory 152. In other words, the setting unit 133 according to the first embodiment can set the display conditions based on the initial settings set in advance. FIG. 10 is a chart illustrating an example of the setting information stored by the setting information memory 152 according to the first embodiment.

For example, as illustrated in FIG. 10, the setting information stored by the setting information memory 152 is information in which the region of interest, the parallax angle, rotation, a rotational speed (deg/s), stop (deg), the direction of rotation, and an initial position (x, y, z) are correlated with each other for each diagnosis region. Here, the diagnosis region represents a region subject to the diagnostic imaging; the region of interest represents a region desired to be displayed by the display unit 120; the parallax angle represents a parallax angle of a parallax image group displayed on the display unit 120; the rotation represents rotation of an image displayed by the display unit 120; the rotational speed (deg/s) represents a rotational speed of the image displayed by the display unit 120; the stop (deg) represents an angle by which the image displayed by the display unit 120 moves from when it starts until it stops rotating; the direction of rotation represents the direction in which the image displayed by the display unit 120 is rotated; and the initial position (x, y, z) represents structural coordinates of the diagnosis region in the volume data displayed in the center of the display unit 120 when the display is started.

For example, the setting information illustrated in FIG. 10 represented as "Diagnosis Region: Lungs, Region of Interest: Mediastinum, Parallax Angle: 1 degree, Rotation: Yes, Rotational Speed (deg/s): 30, Stop (deg): 360, Direction of Rotation: L to R, Initial Position (x, y, z): (0, 100, 0)" means that, in the case of displaying the "mediastinum" of the "lungs", a parallax image group having a "parallax angle" of "1 degree" is generated, and displayed in the initial position at the "coordinates (0, 100, 0)", and rotated "from left to right" at a speed of "30 degrees per second", and stopped after being rotated by "360 degrees".

If, for example, the extracting unit 132 extracts the lung nodule illustrated in FIG. 7C as the area of interest, the setting unit 133 refers to the setting information illustrated in FIG. 10, and sets the display conditions. That is, the setting unit 133 sets the display conditions so as to generate a parallax image group having a "parallax angle" of "2 degrees", to display the parallax image group in the initial position at the "structural coordinates of the lung nodule relative to the lungs in the volume data", to rotate the parallax image group "from left to right" at a speed of "10 degrees per second", and stops it after being rotated by "90 degrees".

As described above, the setting unit 133 sets the display conditions of the parallax image group to be displayed on the display unit 120 depending on the region of interest, and thereby, the X-ray CT apparatus 1 according to the first embodiment can easily display the medical image suitable for image interpretation on the 3D monitor. For example, the X-ray CT apparatus 1 according to the first embodiment makes it possible to set the display conditions in accordance with the anatomical size and the structural complexity of the area of interest.

In the example described above, the case has been described in which the setting unit 133 changes the setting of the parallax angle as the setting regarding the generation of the parallax image group. The setting unit 133 can set, as the setting regarding the generation of the parallax image group, the reconstruction function for image processing, correction processing for the projection data, and reconstruction of the volume data. For example, the setting unit 133 sets a reconstruction function suitable for stereoscopic viewing.

Referring back to FIG. 6, the display controller 134 performs control so as to display on the display unit 120 an editing window for the settings changed by the setting unit 133. That is, the X-ray CT apparatus 1 according to the first embodiment can present the display conditions set by itself to the operator, and allow the operator to edit them. FIG. 11 is a diagram for explaining an example of processing by the display controller 134 according to the first embodiment. For example, as illustrated in FIG. 11, the display controller 134 displays on the display unit 120 the editing window for accepting, from the operator, editing of the settings such as the direction of rotation, the rotational speed (deg/s), the initial position (x, y, z), and the stop (deg). That is, the operator can perform more detailed setting by using the editing window displayed by the display unit 120. Although not illustrated, the X-ray CT apparatus 1 according to the first embodiment can also accept editing by the operator even while the parallax image group is displayed under the display conditions set by the setting unit 133. For example, the X-ray CT apparatus 1 can allow the operator to operate to stop the image from rotating before completion of the rotation.

In the above-described first embodiment, the description has been made by exemplifying the parallax angle, the rotation, the rotational speed, the stop, the direction of rotation, and the initial position as the settings changed by the setting unit 133. However, these are merely examples, and the disclosed technology is not limited to these examples. For example, the enlargement ratio and the contraction ratio of the image, the number and the positions of the virtual light sources, and a detailed setting of the rotational speed are exemplified as other settings changed by the setting unit 133. The detailed setting of the rotational speed is made, for example, in such a manner that the rotational speed is made low so as to enable sufficient observation when the vicinity of the area of interest is displayed, while the rotational speed is made high when areas other than the area of interest are displayed.

Figure 12:
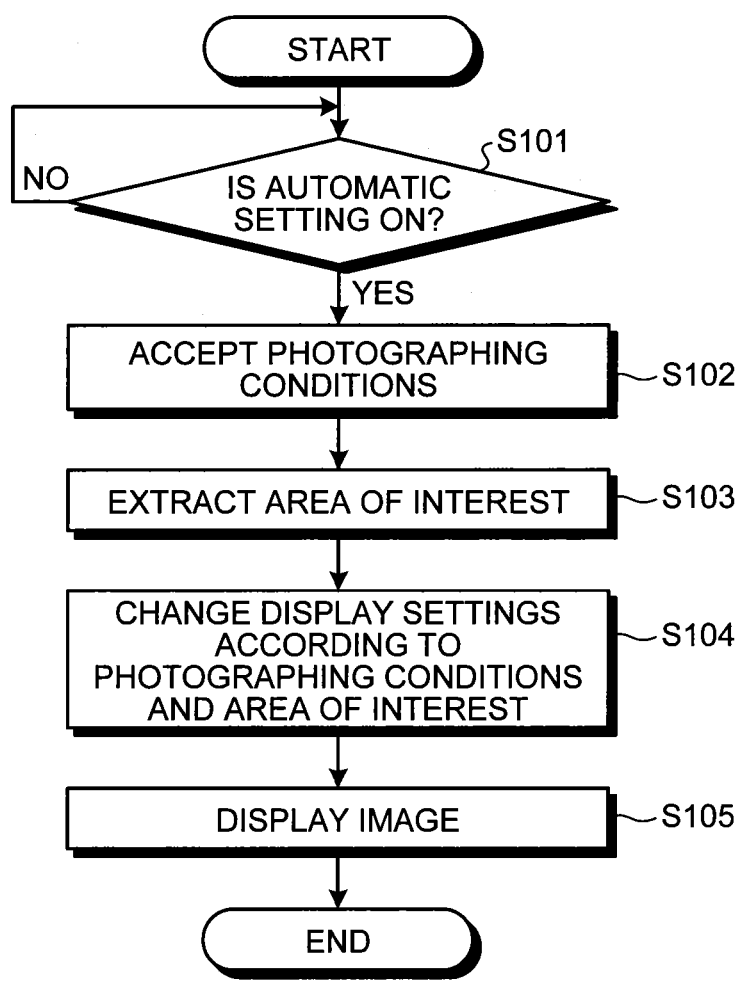
FIG. 12 is a flow chart illustrating a procedure of processing by the X-ray CT apparatus according to the first embodiment.

Next, processing of the X-ray CT apparatus 1 according to the first embodiment will be described using FIG. 12. FIG. 12 is a flow chart illustrating a procedure of the processing by the X-ray CT apparatus 1 according to the first embodiment. As illustrated in FIG. 12, in the X-ray CT apparatus 1 according to the first embodiment, if an automatic setting is ON (Yes at Step S101), the accepting unit 131 accepts photographing conditions (Step S102).

Then, the extracting unit 132 extracts an area of interest based on the photographing conditions accepted by the accepting unit 131 (Step S103). Next, the setting unit 133 changes the display settings of a parallax image group to be displayed on the display unit 120 according to the photographing conditions accepted by the accepting unit 131 and the area of interest extracted by the extracting unit 132 (Step S104). Thereafter, the display unit 120 displays the image according to the settings changed by the setting unit 133 (Step S105), and the processing is terminated.

As described above, according to the first embodiment, the accepting unit 131 accepts the input of the conditions with respect to regions to be photographed and arrangement of the regions. Then, the extracting unit 132 extracts the area of interest of each subject by analyzing the medical image data photographed based on the conditions accepted by the accepting unit 131. Then, based on the conditions and the area of interest extracted by the extracting unit 132, the setting unit 133 sets the display conditions of the parallax image group to be displayed on the display unit 120 having the stereoscopic viewing function. Accordingly, the X-ray CT apparatus 1 according to the first embodiment can set the display conditions depending on the region of interest, and thus makes it possible to easily display a medical image suitable for image interpretation on the monitor for stereoscopic viewing.

According to the first embodiment, the accepting unit 131 also accepts the photographing conditions and the reconstructing conditions as conditions. Then, the extracting unit 132 extracts the area of interest based on the photographing conditions and the reconstructing conditions accepted by the accepting unit 131. Then, the setting unit 133 sets the display conditions based on the photographing conditions and the reconstructing conditions accepted by the accepting unit 131, and on the area of interest extracted by the extracting unit 132. Accordingly, the X-ray CT apparatus 1 according to the first embodiment can set the display conditions based on the detailed conditions, and thus makes it possible to easily display a medical image more suitable for image interpretation on the monitor for stereoscopic viewing.

Also, according to the first embodiment, the setting unit 133 sets, as the display conditions, at least one of the condition regarding the generation of the parallax image group and the conditions regarding the display of the parallax image group. Accordingly, the X-ray CT apparatus 1 according to the first embodiment can automatically change the settings regarding the generation and the display of the parallax image group, and thus makes it possible to easily display a medical image more optimal for image interpretation on the monitor for stereoscopic viewing.

According to the first embodiment, the setting unit 133 also sets the parallax angle of the parallax image group as the condition regarding the generation of the parallax image group. Accordingly, the X-ray CT apparatus 1 according to the first embodiment makes it possible to generate a parallax image group more suitable for stereoscopic viewing.

According to the first embodiment, the setting unit 133 also sets the position and the display direction of the object to be displayed to be represented in the parallax image group as the conditions regarding the display of the parallax image group. Accordingly, the X-ray CT apparatus 1 according to the first embodiment makes it possible to display a parallax image group that can be observed more easily.

Second Embodiment

In the first embodiment described above, the case has been described in which the display conditions are switched between the areas of interest in a simple manner in accordance with the state of display by the display unit 120. In a second embodiment, description will be made of a case of controlling the switching of the display conditions for each area of interest. In the second embodiment, description will be made by denoting a controller for controlling the switching of the display conditions for each area of interest as a display controller 134a. That is, the display controller 134a is provided by adding a new process to the process of the display controller 134 illustrated in FIG. 6.

Figure 13:
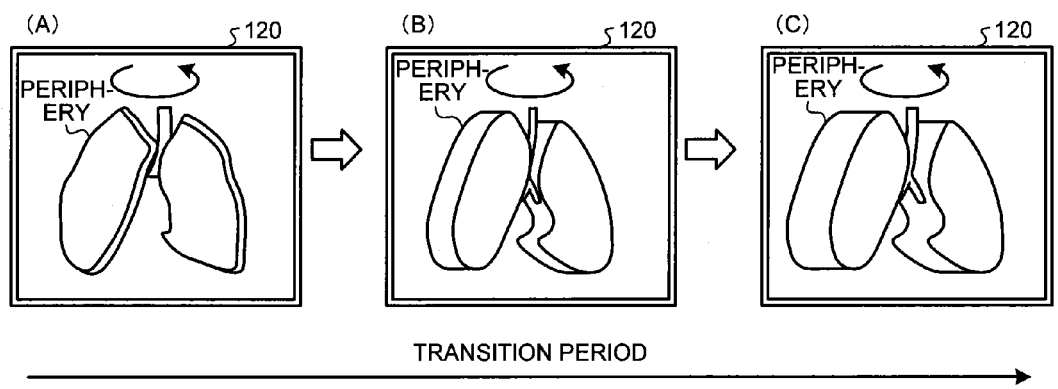
FIG. 13 a diagram for explaining an example of control by a display controller according to a second embodiment.

The display controller 134a switches the display conditions set for each area of interest in a stepwise manner, and, when having accepted a switching request from an operator, instantly switches the display conditions. Specifically, the display controller 134a switches the display conditions for each area of interest, based on a transition period serving as a period for switching the display conditions. FIG. 13 a diagram for explaining an example of the control by the display controller according to the second embodiment.

In FIG. 13, the area of interest is the mediastinum and the peripheries. FIG. 13 illustrates the switching of the display conditions when the mediastinum and the peripheries are respectively displayed on the display unit 120 in the case of displaying the entire lungs while rotating them about the mediastinum as an axis. For example, assume that the parallax angle as a display setting of the mediastinum is set to 1 degree, and the parallax angle as a display setting of the peripheries is set to 3 degrees, and assume that the entire lungs are set to be displayed while being rotated. In such a case, when displaying the mediastinum on the display unit 120, the display controller 134a displays the parallax image group generated with the parallax angle of 1 degree. That is, as illustrated in (A) of FIG. 13, an image having an appearance of relatively small depth is displayed on the display unit 120.

Then, based on the transition period of a predetermined length, the display controller 134a gradually switches the screen from the screen (A) displaying the mediastinum to the screen (C) displaying the peripheries on the display unit 120, as illustrated in FIG. 13. That is, as illustrated in (B) of FIG. 13, the display controller 134a displays the entire lungs while rotating it about the mediastinum as an axis, and displays the parallax image group generated with a gradually increasing parallax angle along with the display of the peripheries on the display unit 120.

Then, at the time when the transition period expires, the display controller 134a displays on the display unit 120 the parallax image group generated with a parallax angle of 3 degrees for the area of the peripheries. That is, as illustrated in (C) of FIG. 13, an image having an appearance of sufficient depth is displayed on the display unit 120. In other words, the operator can view the image with a natural appearance because the image displayed on the display unit 120 is smoothly switched from (A) to (C) in FIG. 13. There may be a case in which the display controller 134a automatically sets the length of the transition period based on the rotational speed of the object to be displayed, or a case in which the operator arbitrarily sets the length of the transition period.

Here, when having accepted the switching request from the operator, the display controller 134a cancels the transition period, and instantly switches the screen from the screen (A) to the screen (C). The switching request from the operator corresponds to, for example, a case in which the operator performs an input operation via the input unit 110 in order to rotate and view the image. In this manner, when, for example, the operator wants to specify a location by oneself and closely examine the location, the operator can instantly switch the display conditions so as to reduce blurring of the image and perform the operation without stress.

As described above, according to the second embodiment, the display controller 134a switches the display conditions set for each area of interest in a stepwise manner, and, when having accepted the switching request from the operator, instantly switches the display conditions. Accordingly, the X-ray CT apparatus 1 according to the second embodiment makes it possible to stereoscopically display a medical image that is easier for the operator to observe.

Third Embodiment

In the first and the second embodiments described above, the cases have been described in which the display conditions of the parallax image group are set in the X-ray CT apparatus 1 serving as the medical image diagnostic apparatus. In a third embodiment, description will be made of a case in which the display conditions of the parallax image group are set in the medical image processing apparatus. The description will be made below of an example of a case of using a workstation as the medical image processing apparatus.

Figure 14:
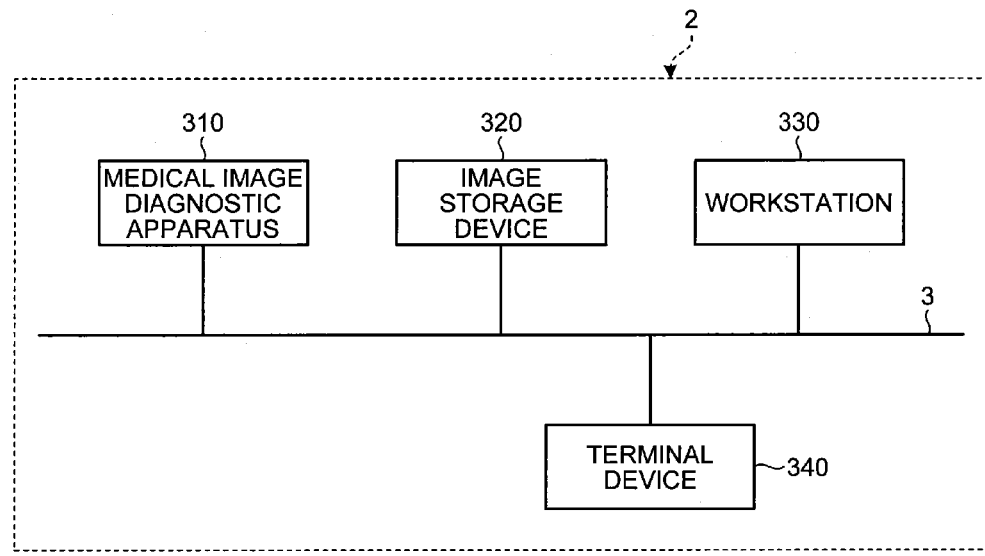
FIG. 14 is a diagram for explaining a configuration example of a medical image processing system according to a third embodiment.

First, description will be made of a configuration of a medical image processing system including the workstation according to the third embodiment. FIG. 14 is a diagram for explaining a configuration example of the medical image processing system according to the third embodiment. As illustrated in FIG. 14, a medical image processing system 2 according to the third embodiment includes a medical image diagnostic apparatus 310, an image storage device 320, a workstation 330, and a terminal device 340. The devices illustrated in FIG. 14 are directly or indirectly communicable with each other, for example, via an in-hospital local area network (LAN) 3 installed in a hospital. For example, if a picture archiving and communication system (PACS) is introduced in the medical image processing system 2, the devices send and receive medical images and the like to and from each other in accordance with the Digital Imaging and Communications in Medicine (DICOM) standard.

The medical image processing system 2 such as described above generates a parallax image group from the volume data serving as three-dimensional medical image data generated by the medical image diagnostic apparatus 310, and displays the parallax image group on a stereoscopically viewable monitor, thus providing a stereoscopically viewable medical image for medical doctors and inspection engineers working in the hospital. Specifically, in the third embodiment, the workstation 330 applies various types of image processing to the volume data and thus generates a parallax image group. Also, the workstation 330 and the terminal device 340 have respective stereoscopically viewable monitors, and display on the monitors the parallax image group generated in the workstation 330. The image storage device 320 stores therein the volume data generated in the medical image diagnostic apparatus 310 and the parallax image group generated in the workstation 330. That is, the workstation 330 and the terminal device 340 obtain the volume data and the parallax image group from the image storage device 320, and process and display on the monitors the obtained data. The devices will be described below in sequence.

The medical image diagnostic apparatus 310 is, for example, an X-ray diagnostic apparatus, an X-ray computed tomography (CT) apparatus, a magnetic resonance imaging (MRI) apparatus, an ultrasonic diagnostic apparatus, a single photon emission computed tomography (SPECT) apparatus, a positron emission computed tomography (PET) apparatus, a SPECT-CT apparatus in which a SPECT apparatus and an X-ray CT apparatus are integrated with each other, a PET-CT apparatus in which a PET apparatus and an X-ray CT apparatus are integrated with each other, or a group of these apparatuses. The medical image diagnostic apparatus 310 according to the third embodiment can generate three-dimensional medical image data (volume data).

Specifically, the medical image diagnostic apparatus 310 according to the third embodiment generates volume data by photographing a subject. For example, the medical image diagnostic apparatus 310 collects data, such as projection data or MR signals, by photographing a subject, and from the collected data, reconstructs medical image data in a plurality of axial planes along the direction of body axis of the subject, thereby generating volume data. The medical image diagnostic apparatus 310 reconstructs, for example, medical image data of 500 axial planes. This medical image data group of the 500 axial planes is the volume data. The volume data may also be constituted by the data itself, such as the projection data or the MR signals, of the subject photographed by the medical image diagnostic apparatus 310.

The medical image diagnostic apparatus 310 according to the third embodiment also sends the generated volume data to the image storage device 320. When sending the volume data to the image storage device 320, the medical image diagnostic apparatus 310 sends, as supplementary information, for example, a patient ID identifying a patient, an inspection ID identifying an inspection, an apparatus ID identifying the medical image diagnostic apparatus 310, and a series ID identifying one shot of photographing by the medical image diagnostic apparatus 310.

The image storage device 320 is a database that stores therein the medical images. Specifically, the image storage device 320 according to the third embodiment contains the volume data sent from the medical image diagnostic apparatus 310 in a memory and stores the volume data therein. In addition, in the third embodiment, the workstation 330 generates a parallax image group from the volume data, and sends the generated parallax image group to the image storage device 320. Accordingly, the image storage device 320 contains the parallax image group sent from the workstation 330 in the memory, and stores the parallax image group therein. The present embodiment may be a case in which the workstation 330 and the image storage device 320 illustrated in FIG. 14 are integrated with each other by using a type of the workstation 330 that can store large-capacity images. In other words, the present embodiment may be a case in which the workstation 330 itself stores therein the volume data or the parallax image group.

In the third embodiment, the volume data and the parallax image group are stored in the image storage device 320 in a corresponding manner to, for example, the patient ID, the inspection ID, the apparatus ID, and the series ID. Accordingly, the workstation 330 and the terminal device 340 obtain the necessary volume data and the necessary parallax image group from the image storage device 320 by performing a search using, for example, the patient ID, the inspection ID, the apparatus ID, and the series ID.

The workstation 330 is an image processing apparatus that applies image processing to the medical image. Specifically, the workstation 330 according to the third embodiment applies various types of rendering processing to the volume data obtained from the image storage device 320, and thus generates a parallax image group. The parallax image group refers to a plurality of images photographed from a plurality of viewpoints. For example, a parallax image group displayed on a monitor that enables the nine-parallax image to be stereoscopically viewed by naked eyes refers to nine images whose viewpoint positions differ from each other.

The workstation 330 according to the third embodiment includes as a display unit the stereoscopically viewable monitor. The workstation 330 generates a parallax image group, and displays the generated parallax image group on the stereoscopic display monitor. As a result, the operator of the workstation 330 can perform operations for generating the parallax image group while checking the stereoscopically viewable medical image displayed on the stereoscopic display monitor.

The workstation 330 also sends the generated parallax image group to the image storage device 320. When sending the parallax image group to the image storage device 320, the workstation 330 additionally sends, as supplementary information, for example, the patient ID, the inspection ID, the apparatus ID, and the series ID. The supplementary information sent when the parallax image group is sent to the image storage device 320 includes also supplementary information related to the parallax image group. The supplementary information related to the parallax image group includes, for example, the number of parallax images (e.g., 9) and a resolution (e.g., 466×350 pixels).

Here, the workstation 330 according to the third embodiment changes the settings of the parallax image group according to the photographing conditions and the area of interest so as to make it possible to easily display an optimal medical image for image interpretation on the monitor for stereoscopic viewing. This point will be described later in detail.

The terminal device 340 is a device for allowing the medical doctors and the inspection engineers working in the hospital to view the medical images. For example, the terminal device 340 is a personal computer (PC), a tablet PC, a personal digital assistant (PDA), a cellular phone, or the like that is operated by the medical doctors and the inspection engineers working in the hospital. Specifically, the terminal device 340 according to the third embodiment includes a stereoscopic display monitor as a display unit. The terminal device 340 obtains the parallax image group from the image storage device 320, and displays the obtained parallax image group on the stereoscopic display monitor. As a result, the medical doctor or the inspection engineer acting as an observer can view the stereoscopically viewable medical image.

So far, the configuration example of the medical image processing system 2 according to the third embodiment has been briefly described. Note that the application of the medical image processing system 2 described above is not limited to the case in which the PACS is introduced therein. For example, the medical image processing system 2 is also applied in the same manner to a case in which an electronic chart system that manages electronic charts attached with medical images is introduced. In this case, the image storage device 320 is a database that stores therein the electronic charts. Moreover, the medical image processing system 2 is also applied in the same manner, for example, to a case in which a hospital information system (HIS) or a radiology information system (RIS) is introduced. Also, the medical image processing system 2 is not limited to the above-described configuration example. The functions included in the devices and distribution thereof may be changed as appropriate depending on the mode of operations.

Figure 15:
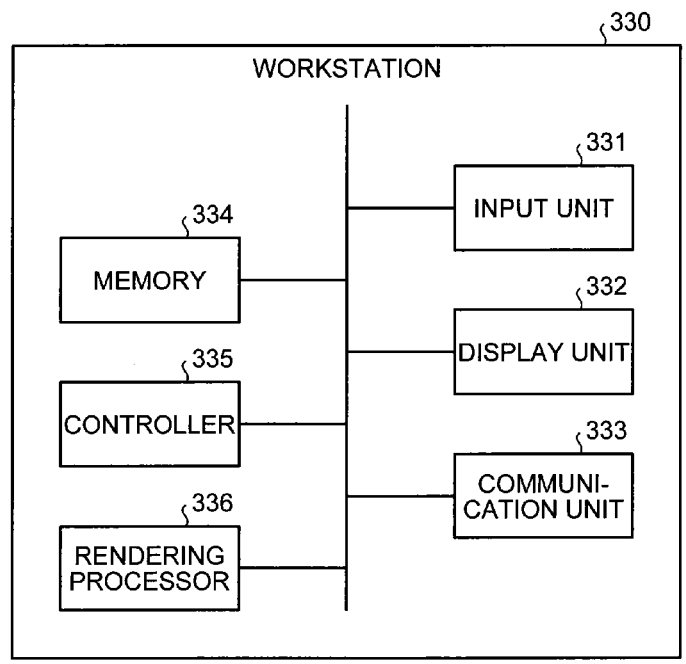
FIG. 15 is a diagram for explaining a configuration example of a workstation according to the third embodiment.

Next, a configuration example of the workstation according to the third embodiment will be described using FIG. 15. FIG. 15 is a diagram for explaining the configuration example of the workstation 330 according to the third embodiment.

The workstation 330 according to the third embodiment is a high-performance computer suitable for image processing and so on, and as illustrated in FIG. 15, includes an input unit 331, a display unit 332, a communication unit 333, a memory 334, a controller 335, and a rendering processor 336. Although description will be made below using a case in which the workstation 330 is a high-performance computer suitable for image processing and so on, the workstation 330 is not limited to this case, and may be any information processing device. For example, the workstation 330 may be any personal computer.

The input unit 331 includes, for example, a mouse, a keyboard, and a trackball, and accepts input of various operations for the workstation 330 from the operator. Specifically, the input unit 331 according to the third embodiment accepts input of information for obtaining the volume data to be subjected to the rendering processing from the image storage device 320. For example, the input unit 331 accepts input of, for example, the patient ID, the inspection ID, the apparatus ID, and the series ID. The input unit 331 according to the third embodiment also accepts input of conditions related to the rendering processing (hereinafter called rendering conditions).

The display unit 332 is, for example, a liquid crystal panel serving as the stereoscopic display monitor, and displays various types of information. Specifically, the display unit 332 according to the third embodiment displays, for example, graphical user interfaces (GUIs) for accepting various operations from the operator and the parallax image group. The communication unit 333 is, for example, a network interface card (NIC), and performs communication with other devices.

The memory 334 is, for example, a hard disk or a semiconductor memory device, and stores therein various types of information. Specifically, the memory 334 according to the third embodiment stores therein the volume data obtained from the image storage device 320 via the communication unit 333. The memory 334 according to the third embodiment also stores therein, for example, the volume data while being processed by the rendering processing and the parallax image group generated by the rendering processing. The memory 334 further stores therein setting information that serves as information regarding the generation of the parallax image group and that is used by the controller 335 to be described later. The setting information stored by the memory 334 will be described later in detail.

The controller 335 is an electronic circuit such as a central processing unit (CPU) or a micro processing unit (MPU), or an integrated circuit such as an application specific integrated circuit (ASIC) or a field programmable gate array (FPGA), and performs overall control of the workstation 330.

For example, the controller 335 according to the third embodiment controls the display of the GUIs and the display of the parallax image group for the display unit 332. The controller 335 also controls, for example, sending and receiving of the volume data and the parallax image group to and from the image storage device 320 via the communication unit 333. The controller 335 further controls, for example, the rendering processing performed by the rendering processor 336. The controller 335 still further controls, for example, reading of the volume data from the memory 334, and storing of the parallax image group into the memory 334.

Figure 16:
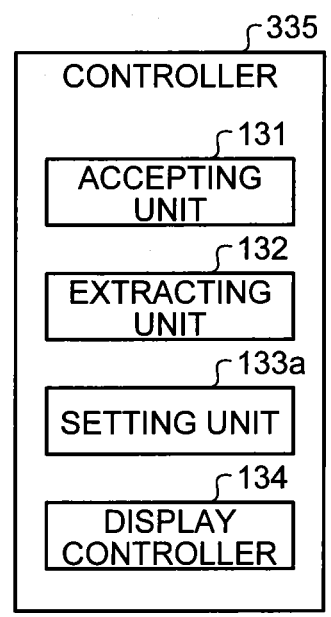
FIG. 16 is a diagram illustrating a configuration example of a controller according to the third embodiment.

Here, in the third embodiment, the controller 335 of the workstation 330 controls the rendering processing by the rendering processor 336 and the display of the parallax image group by the display unit 332. Description of the rendering processor 336 is omitted because it performs the same processing as that of the rendering processor 142 described in the first embodiment. FIG. 16 is a diagram illustrating a configuration example of the controller 335 according to the third embodiment.

As illustrated in FIG. 16, the controller 335 includes the accepting unit 131, the extracting unit 132, a setting unit 133a, and the display controller 134. Note that, in the controller 335 according to the third embodiment, the same reference numeral is given to the processing unit performing the same processing as that of the processing unit in the system controller 130 according to the first embodiment. That is, only the content of processing by the setting unit 133a differs in the controller 335 according to the third embodiment. The following description will focus on this processing.

The setting unit 133a refers to the setting information stored by the memory 334, and changes the settings of the parallax image group to be displayed on the display unit 332. Here, the setting information referred to by the setting unit 133a will be described. FIG. 17 is a chart illustrating an example of the setting information stored by the memory 334 according to the third embodiment.

For example, as illustrated in FIG. 17, the setting information stored by the memory 334 is information in which the diagnosis region, the region of interest, the parallax angle, the rotation, the rotational speed (deg/s), the stop (deg), the direction of rotation, and the initial position (x, y, z) are correlated with each other for each modality.

That is, the setting unit 133a determines the setting information to be referred to, based on the information on the modality attached to the medical image data. Thereafter, the setting unit 133a changes the settings of the parallax image group according to the photographing conditions and the area of interest. Description of the change of the settings of the parallax image group is omitted because it is the same processing as that of the setting unit 133 according to the first embodiment.

Figure 18:
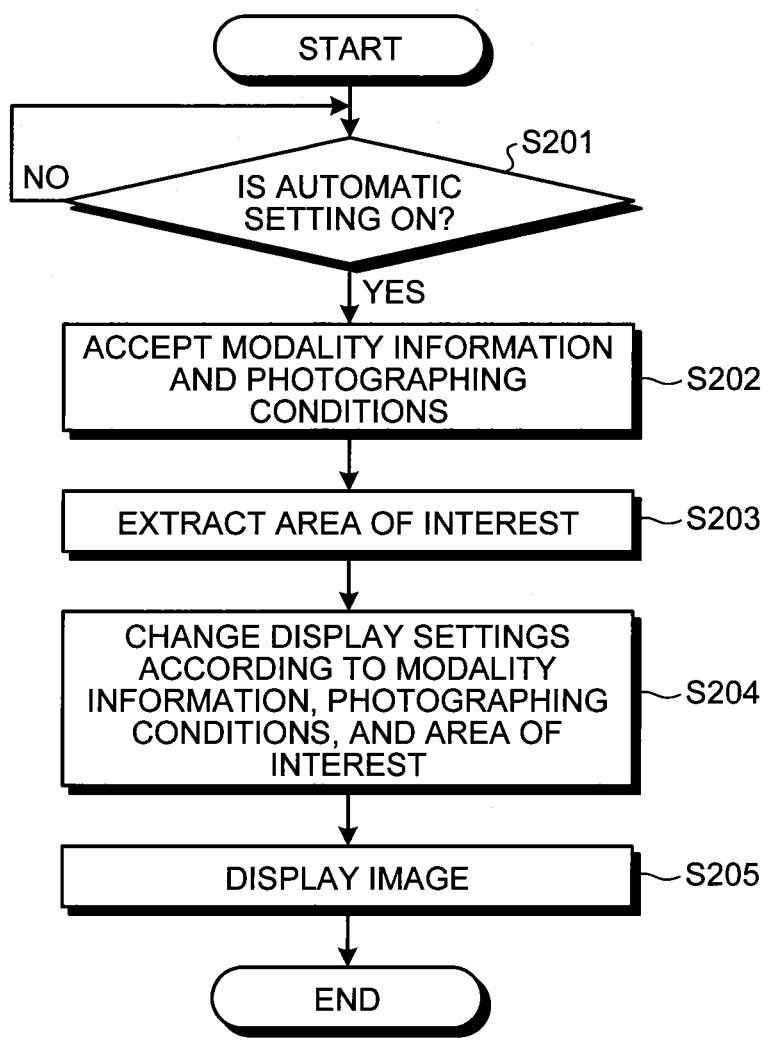
FIG. 18 is a flow chart for explaining processing by the workstation according to the third embodiment.

Next, processing by the workstation 330 according to the third embodiment will be described using FIG. 18. FIG. 18 is a flow chart for explaining the processing by the workstation 330 according to the third embodiment. As illustrated in FIG. 18, in the workstation 330 according to the third embodiment, if an automatic setting is ON (Yes at Step S201), the accepting unit 131 accepts the modality information and the photographing conditions (Step S202).

Then, the extracting unit 132 extracts an area of interest based on the photographing conditions accepted by the accepting unit 131 (Step S203). Next, the setting unit 133a changes the display settings of the parallax image group to be displayed on the display unit 332 according to the modality information and the photographing conditions accepted by the accepting unit 131 and to the area of interest extracted by the extracting unit 132 (Step S204). Thereafter, the display unit 332 displays the image according to the settings changed by the setting unit 133a (Step S205), and the processing is terminated.

As described above, according to the third embodiment, the setting unit 133a sets the conditions regarding the generation and the display of the parallax image group, based on the information on the modality by which the medical image has been photographed, the photographing conditions, and the area of interest extracted by the extracting unit 132. Accordingly, the workstation 330 according to the third embodiment makes it possible to perform setting for generation and display of the parallax image group with diagnostic characteristics of each modality taken into consideration Fourth Embodiment While the first, the second, and the third embodiments have been described so far, various different embodiments may be implemented in addition to the first, the second, and the third embodiments described above.

In each of the first, the second, and the third embodiments, the description has been made of the processing applied to a single piece of volume data. However, embodiments are not limited to this case, and may include a case of processing, for example, volume data (4D data) collected over time by photographing a moving organ, such as a heart or lungs, as a photographing target region. Description will be made below of an example of the processing by the X-ray CT apparatus 1 using the 4D data of a heart.

In such a case, for example, the setting unit 133 makes the image processor 140 reconstruct an X-ray CT image in synchronization with a waveform of an electrocardiogram (ECG) (hereinafter mentioned as "synchronous reconstruction"). More specifically, the setting unit 133 makes the image processor 140 generate volume data in synchronization with the waveform of the electrocardiogram, and makes various settings for rendering processing applied to each piece of the volume data generated over time. For example, to display the heart while rotating it, the setting unit 133 makes settings so that the rendering processing from a different viewpoint position is applied to each piece of the volume data generated over time.

Figure 19:
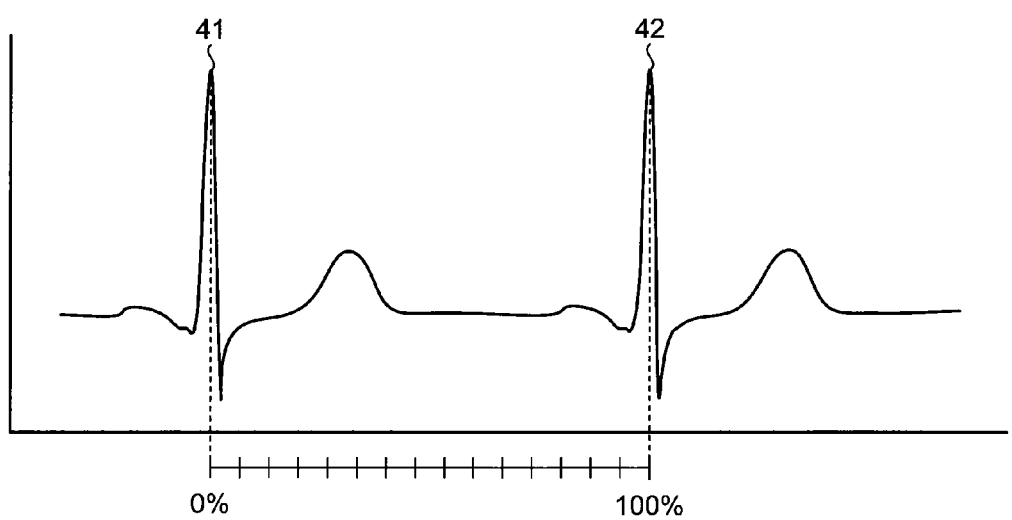
FIG. 19 is a diagram for explaining an example of synchronous reconstruction according to a fourth embodiment.

Here, the synchronous reconstruction will be described using FIG. 19. FIG. 19 is a diagram for explaining an example of the synchronous reconstruction according to a fourth embodiment. Note that the horizontal axis in FIG. 19 represents time. For example, assuming the phase between R waves to be 100%, the setting unit 133 makes the image processor 140 generate volume data at each interval of a predetermined phase, and makes settings for the rendering processing applied to each piece of the volume data. To take an example, as illustrated in FIG. 19, the setting unit 133 assumes the position of an R wave 41 to be 0% and the position of an R wave 42 to be 100% in the waveform of the electrocardiogram, and divides the phase between those positions into predetermined intervals.

Then, the setting unit 133 makes the image processor 140 apply the rendering processing from a different viewpoint position to each piece of the volume data corresponding to each of the divided phases so as to generate a parallax image group with an angle different by a predetermined value. For example, as illustrated in FIG. 19, the setting unit 133 divides the interval between the R waves into 15 phases, and makes the image processor 140 generate volume data at each interval of the divided phase (%) and apply the rendering processing to each piece of the generated volume data while shifting the viewpoint position at intervals of 24 degrees. Thus, the setting unit 133 makes the image processor 140 generate a parallax image group.

Then, the display controller 134 makes the display unit 120 display the parallax image group of each phase generated based on the settings made by the setting unit 133 while updating the parallax image group at predetermined time intervals. Consequently, the image displayed on the display unit 120 results in an image of a rotating heart with motion (pulsation). While the case of rotating the heart has been described in the example described above, the embodiment is not limited to this case. For example, the image generated at each phase can be enlarged or contracted. While the case of using the X-ray CT apparatus 1 has been described in the example described above, the embodiment is not limited to this case, and may include a case of using the workstation 330.

In each of the first and the second embodiments described above, the case has been described in which the X-ray CT apparatus is used as the medical image diagnostic apparatus. However, the disclosed technology is not limited to this case, and may be applied to, for example, a case of using the MRI apparatus, the ultrasonic diagnostic apparatus, the PET-CT apparatus, or a PET-MR apparatus as the medical image diagnostic apparatus.

In each of the first, the second, and the third embodiments, the case has been described in which the memory stores therein the setting information. However, the disclosed technology is not limited to this case. The setting information may be, for example, built into an expert plan.

In each of the first, the second, and the third embodiments, the case has been described in which the organ (lungs) is used as a region to be photographed. However, the disclosed technology is not limited to this case, and may be applied to, for example, a case of using a bone structure as the region to be photographed. To take an example, the disclosed technology may be used in the case of performing a bone fracture examination.

As described above, according to the first to fourth embodiments, an optimal medical image for image interpretation can be displayed on the monitor for stereoscopic viewing.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A medical image diagnostic apparatus, comprising:
processing circuitry configured to
accept input of conditions with respect to diagnosis regions to be scanned and arrangement of the diagnosis regions in volume data;
extract a region of interest that is set according to the diagnosis regions by analyzing the volume data acquired based on the accepted conditions and determine a portion of the extracted region of interest in the diagnosis regions;
set each generating condition of a plurality of parallax image groups that are generated from the volume data to display the diagnosis regions while rotating the diagnosis regions and a condition with respect to the rotation and stopping of the diagnosis regions, based on the arrangement of the diagnosis regions in the volume data, the position of the extracted region of interest in the diagnosis regions, and a type of the extracted region of interest; and
perform control to display the plurality of parallax image groups generated by each generating condition on a display having a stereoscopic viewing function, based on the condition with respect to the rotation and the stopping of the diagnosis regions.

2. The medical image diagnostic apparatus according to claim 1, wherein
the processing circuitry accepts scanning conditions and reconstructing conditions as the accepted conditions,
the processing circuitry extracts the region of interest based on the accepted scanning conditions and the accepted reconstructing conditions, and
the processing circuitry sets each generating condition and the condition with respect to the rotation and stopping of the diagnosis regions based on the accepted scanning conditions and the accepted reconstructing conditions and based on the extracted region of interest.

3. The medical image diagnostic apparatus according to claim 1, wherein the processing circuitry sets a parallax angle of each of the parallax image groups, respectively, as the generating condition of each of the parallax image groups.

4. The medical image diagnostic apparatus according to claim 1, wherein the processing circuitry sets, as the condition with respect to the rotation and stopping of the diagnosis regions, a start position of the rotation, a stop position of the rotation, a rotational speed, and a direction of rotation.

5. The medical image diagnostic apparatus according to claim 1, wherein the processing circuitry determines, based on scanning conditions, a structure of the diagnosis regions included in the volume data, determines a relative position of the extracted region of interest in the determined structure of the diagnosis regions, and sets the condition with respect to the rotation and stopping of the diagnosis regions so that an image including the determined relative position of the region of interest is displayed on the display.

6. The medical image diagnostic apparatus according to claim 1, wherein the processing circuitry is further configured to switch in a stepwise manner the set generating condition and the condition with respect to the rotation and stopping of the diagnosis regions for each of the regions of interest, and when having accepted a switching request from an operator, instantly switch the generating condition and the condition with respect to the rotation and stopping of the diagnosis regions.

7. A medical image processing method, comprising:
accepting input of conditions with respect to diagnosis regions to be scanned and arrangement of the diagnosis regions in volume data;
extracting a region of interest that is set according to the diagnosis regions by analyzing the volume data acquired based on the accepted conditions and determining a position of the extracted region of interest in the diagnosis regions; and
setting each generating condition of a plurality of parallax image groups that are generated from the volume data to display the diagnosis regions while rotating the diagnosis regions and a condition with respect to the rotation and stopping of the diagnosis regions, based on the arrangement of the diagnosis regions in the volume data, the position of the extracted region of interest in the diagnosis regions, and a type of the extracted region of interest; and performing control to display the plurality of parallax image groups generated by each generating condition on a display having a stereoscopic viewing function, based on the condition with respect to the rotation and the stopping of the diagnosis regions.

\* \* \* \* \*